United States Patent

Nagai et al.

[11] Patent Number: 5,079,002
[45] Date of Patent: Jan. 7, 1992

[54] HEMOLYSIS DEPRESSANT AND PLASTICIZER

[75] Inventors: Hirofumi Nagai, Fuji; Yoshinori Kubota, Tokyo; Youko Tamura, Fuji; Akio Kimura, Wakayama, all of Japan

[73] Assignees: Terumo Kabushiki Kaisha; Kao Corporation, both of Tokyo, Japan

[21] Appl. No.: 391,502

[22] PCT Filed: Jan. 11, 1988

[86] PCT No.: PCT/JP88/00020

§ 371 Date: Jul. 12, 1989

§ 102(e) Date: Jul. 12, 1989

[87] PCT Pub. No.: WO88/05302

PCT Pub. Date: Jul. 28, 1988

[30] Foreign Application Priority Data

| Jan. 13, 1987 | [JP] | Japan | 62-4119 |
| Jan. 13, 1987 | [JP] | Japan | 62-4120 |
| Apr. 23, 1987 | [JP] | Japan | 62-100688 |
| Nov. 9, 1987 | [JP] | Japan | 62-280987 |
| Nov. 9, 1987 | [JP] | Japan | 62-280988 |
| Nov. 9, 1987 | [JP] | Japan | 62-280989 |
| Nov. 9, 1987 | [JP] | Japan | 62-280990 |

[51] Int. Cl.⁵ .................................................. A01N 1/00
[52] U.S. Cl. .................................. 424/400; 424/486; 514/533; 435/2
[58] Field of Search ............... 514/822, 533; 424/400, 424/486; 435/2

[56] References Cited

U.S. PATENT DOCUMENTS

| 4,254,104 | 3/1981 | Suzuki | 424/70 |
| 4,326,025 | 4/1982 | Buckles | 424/101 |
| 4,375,509 | 3/1983 | Buckles et al. | 435/2 |
| 4,401,758 | 8/1983 | Lormeau et al. | 514/822 |
| 4,495,312 | 1/1985 | Hata | 523/105 |
| 4,678,808 | 7/1987 | Ward et al. | 514/822 |
| 4,713,402 | 12/1987 | Solomon | 514/822 |
| 4,769,318 | 9/1988 | Hamasaki et al. | 435/2 |

FOREIGN PATENT DOCUMENTS

| 57-28145 | 2/1982 | Japan . |
| 58-32647 | 2/1983 | Japan . |
| 58-53937 | 3/1983 | Japan . |
| 58-167638 | 10/1983 | Japan . |
| 59-74148 | 4/1984 | Japan . |
| 59-108053 | 6/1984 | Japan . |
| 59-168012 | 9/1984 | Japan . |
| 61-2864 | 1/1986 | Japan . |

OTHER PUBLICATIONS

Brewster & McEwen, Organic Chemistry 3rd Edition, pp. 251–252.

*Primary Examiner*—James J. Seidleck
*Attorney, Agent, or Firm*—Burns, Doane, Swecker & Mathis

[57] ABSTRACT

A hemolysis depressant and a plasticizer each comprising a triglyceride compound. Resin compositions for medical appliances, medical implements and blood preserving liquid using the triglyceride compound as a hemolysis depressant are capable of preventing the blood held in contact therewith from the phenomenon of hemolysis by the activity of the compound in protecting erythrocytes. Vinyl chloride type resin compositions for medical appliances and medical implement using the compound as a plasticizer are substantially deviced of toxicity and offers extremely high safety.

6 Claims, 3 Drawing Sheets

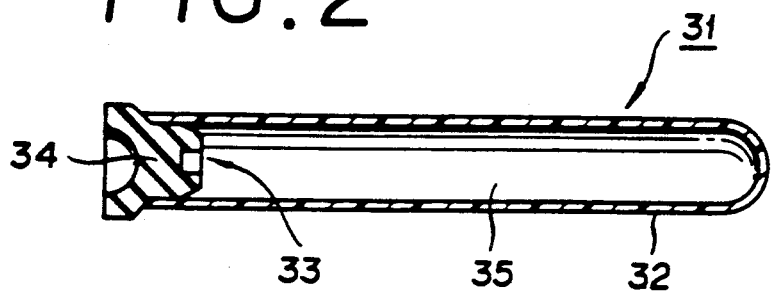
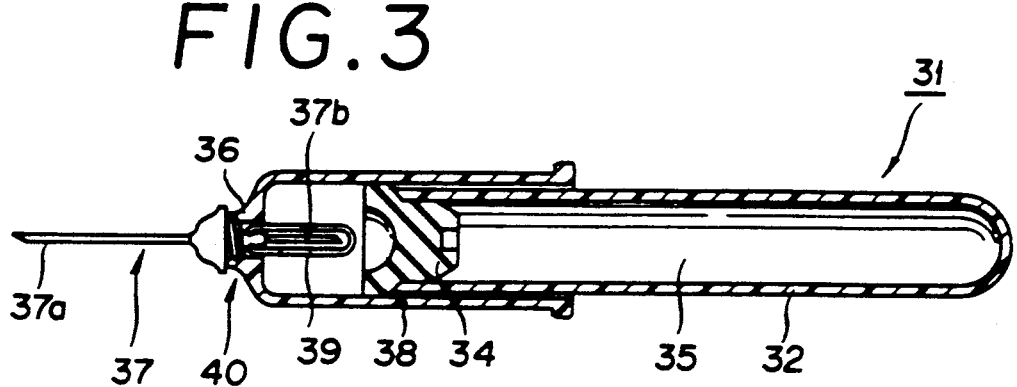
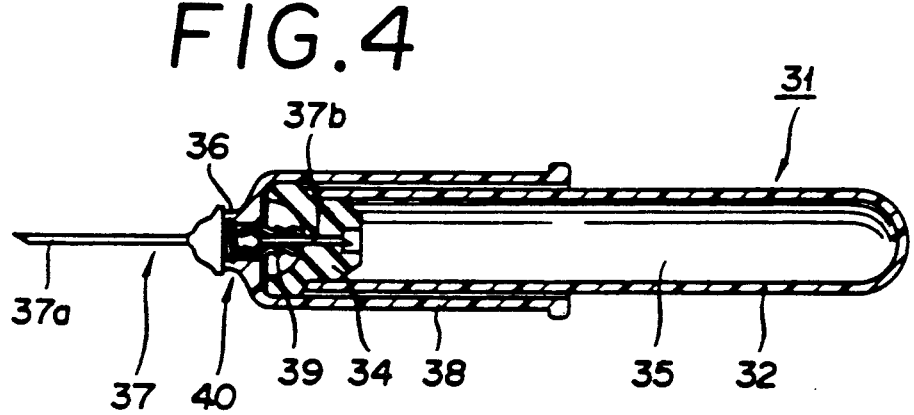

HEMOLYSIS DEPRESSANT AND PLASTICIZER

BACKGROUND OF THE INVENTION

1. Technical Field

This invention relates to a hemolysis depressant and a plasticizer. More particularly, this invention relates to a hemolysis depressant exhibiting extremely high safety and permitting highly effective control of the phenomenon of hemolysis which possibly occurs in blood while in storage and to a resin composition for medical appliances, medical implements and blood preserving liquids which make use of the hemolysis depressant, to a plasticizer exhibiting no toxicity and possessing highly desirable compatibility with vinyl chloride type resins and to vinyl chloride type resin composition for medical appliances and medical implements which make use of the plasticizer. Background Art:

When blood flows out of the blood vessel, it begins to show a visible sign of coagulation within 10 to 20 minutes' exposure to the ambience. The clot which is formed by the coagulation is the final product of a series of chemical reactions which proceed during the conversion of fibrinogen into fibrin. The fibrin are interconnected and, during the course of the interconnection, erythrocytes are entrapped in the clot. In order for the blood for transfusion to retain its original liquid state, therefore, a measure to preclude the normal reactions responsible for the hemal coagulation must be taken during the extraction of the blood from a donor. Heretofore, the practice of adding a liquid anticoagulant as a blood preserving liquid to the freshly extracted blood has been in vogue. The liquid anticoagulant which is in popular use nowadays is intended to effect the preclusion of the hemal coagulation by chelating the calcium ion which constitutes an important factor during the course of coagulation.

Incidentally, the blood for transfusion secured as described above is treated, when necessary, for separation of some of the components thereof and then is placed as in a blood bag, for example, to be preserved until use. When whole blood or a blood component such as concentrated red cells (CRC) is preserved for a long time, there ensues the so-called hemolysis, i.e. a phenomenon which involves external liberation of hemoglobin from the erythrocyte. As main causes for the hemolysis, there can be cited the change in the pressure of osmosis due to a difference in the ion composition in the blood, the difference in the pressure of colloidal osmosis due to such proteinaceous components as hemoglobin, the change in membrane proteins and lipids of erythrocytes, the hindrance to the active transport of $Na^+$ and $K^+$ and the actions of medicines and poisons. The most important factor consists in the liquid anticoagulant to be used. Thus, numerous efforts have been devoted to improve the liquid anticoagulants. All the liquid anticoagulants currently in use are claimed to produce an anticoagulant action and an action for protection of erythrocytes as well. In the liquid anticoagulants of this type, however, the function as a protector for erythrocytes has not yet reached a point where it deserves to be called sufficient.

It is likewise important that the container such as the blood bag for preserving the collected blood should be inactive to blood components. In the blood containers and other similar medical implements which are currently in use, those made of flexible vinyl chloride resin are predominant. The di-2-ethylhexyl phthalate (DOP) which is contained as a plasticizer in the flexible vinyl chloride resin for such medical implements possesses a large capacity for migration. It is known that when the flexible vinyl chloride resin is exposed to blood, the di-2-ethylhexyl phthalate exudes from the container wall and dissolves into the blood (The Japanese Journal of Medical Instrumentation, 54, 221 (1984)). It has been reported that this di-2-ethylhexyl phthalate hinders the aggregating ability of platelets (Journal of Japan Society of Blood Transfusion, 28(3) 282 (1981)). When the preserving container made of such flexible vinyl chloride resin as described above is used to preserve blood, for example, there is the possibility that the di-2-ethylhexyl phthalate will enter the donee's blood vessel as entrained by the preserved blood during the course of transfusion. This possibility poses a problem from the standpoint of the adverse effect exerted by this compound upon the function of platelets.

For the solution of this problem, the feasibility of the use of a material not containing this di-2-ethylhexyl phthalate has been studied. It has been learnt that when blood is preserved in containers made of materials not containing di-2-ethylhexyl phthalate, the erythrocytes in the preserved blood are hemolyzed during the course of preservation. A search of the cause for this hemolysis has revealed that di-2-ethylhexyl phthalate is effective in hindering hemolysis (Blood, 646 1270-(1984)). In other words, when blood is preserved in a blood container made of the conventional flexible vinyl chloride resin which incorporates therein di-ethylhexyl phthalate as a plasticizer, the di-2-ethylhexyl phthalate dissolving into the preserved blood serves to hinder the hemolysis of erythrocytes.

As a measure against such an adverse phenomenon as described above, a contradictory method which comprises preserving blood in a container made of a material incapable of exuding an incorporated plasticizer (or a material not containing any plasticizer) and, prior to actual use of the preserved blood, adding di-2-ethylhexyl phthalate to the blood thereby preventing the blood from hemolysis has been proposed (U.S. Pat. No. 6,326,025). The idea of using di-2-ethylhexyl phthalate as a hemolysis depressant, however, is nothing desirable from the standpoint of physiological safety.

Further, the blood bag containing the blood extracted from a donor is generally forwarded to a hospital, as accompanied by a blood collection tube containing the same blood as that in the blood bag so that the blood in the tube may be used as a sample for testing the blood for adaptability to the patient's blood in advance of the transfusion. As the time of storage of this blood bag increases to approach the 21st day of extraction fixed officially (in Japan) for the availability of concentrated red cells, the blood contained in the blood collection tube yields to hemolysis in much the same way as described above. The hemoglobin liberated in consequence of the hemolysis brings about adverse effects on the results of various measurements performed for clinical test and interferes with the test. This fact has been posed as a problem.

As clearly gathered from the observations illustrated above, the desirability of developing a material capable of producing a notable protective action for erythrocytes has found enthusiastic recognition in various fields including the medical field.

At present, flexible vinyl chloride resins are widely used not only in medical appliances but also in food containers on account of their desirability in terms of moldability, flexibility, transparency, resistance to heat, and cost. For their feasibility in such food containers, the question of toxicity matters much. For this reason, the soft vinyl chloride resins used in the food containers generally incorporate therein as a plasticizer di-2-ethylhexyl phthalate which is accepted as a relatively safe compound in all the known plasticizers. Incidentally, di-2-ethylhexyl phthalate has been demostrated to possess a high migrating property and mono-2-ethylhexyl phthalate (MEHP), a metabolite of di-2-ethylhexyl phthalate, to possess mutagenicy [Yagi et al., Teratology, 14, 259 (1976)]. In view of the defective properties exhibited as described above by the conventional plasticizers coupled with the poor abilities manifested thereby in the control of the phenomenon of coagulation of blood platelets, the desirability of perfecting a safe substance capable of taking the place of di-2-ethylhexyl phthalate as a plasticizer has been finding enthusiastic recognition.

An object of this invention, therefore, is to provide novel hemolysis depressant and plasticizer. Another object of this invention is to provide a resin composition for medical appliances, medical implements, and blood preserving liquids which make use of the novel hemolysis depressant. A further object of this invention is to provide vinyl chloride type resin compositions for medical appliances and medical implements which make use of the novel plasticizer.

This invention also aims to provide a hemolysis depressant capable of providing highly effective control of the phenomenon of hemolysis which occurs in blood during the course of preservation. Further, this invention aims to provide a hemolysis depressant which excels also in physiological safety. This invention also aims to provide a hemolysis depressant which can be incorporated in a resin composition or directly added to a liquid containing erythrocytes.

Further, this invention aims to provide a medical resin composition capable of very effectively controlling the phenomenon of hemolysis in a erythrocyte-containing liquid held in contact with the resin composition. This invention also aims to provide a flexible type medical resin composition which contains no plasticizer or contains substantially nonextractable plasticizer, excels in physiological safety and produces a highly desirable effects in the inhibition of hemolysis, and suits best as a material for medical implements such as the blood bag. This invention further aims to provide a rigid type medical resin composition which produces a highly desirable effect in the inhibition of hemolysis and suits most as a material for such medical implements as the blood collection tube.

In addition, this invention aims to provide a medical implement capable of preserving blood components represented by the erythrocyte in a erythrocyte-containing liquid intact for a long time. This invention further aims to provide a medical implement abounding with physiological safety.

This invention further aims to provide a blood preserving liquid which possesses a highly desirable ability to preserve erythrocytes and abounds with safety. This invention also aims to provide a blood preserving liquid which permits protracted preservation of blood. Further, this invention aims to provide a blood preserving liquid which can be used as a liquid preserver in the anticoagulant and the additive system.

From another aspect, the present invention has as one object thereof the provision of a plasticizer which exhibits no toxicity and possesses highly desirable compatibility and plasticizing efficiency relative to vinyl chloride type resins.

Another object of this invention is to provide vinyl chloride type resin compositions for medical appliances and medical implements which exhibit high physiological safety.

Still another object of this invention is to provide vinyl chloride type resin compositions for medical appliances and medical implements which possess thermal stability enough to withstand sterilization in an autoclave and high transparency, flexibility, and processibility. Disclosure of the Invention:

The various objects described above are accomplished by hemolysis depressant comprising a triglyceride compound represented by the general formula (I):

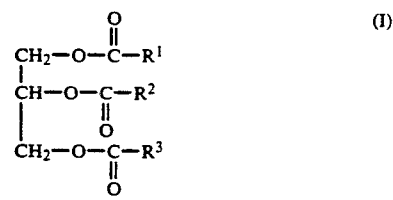

wherein $R^1$, $R^2$, and $R^3$ are independently an aliphatic hydrocarbon group of 1 to 20 carbon atoms and the total number of the carbon atoms of $R^1$, $R^2$, and $R^3$ is in the range of 10 to 36.

This invention also discloses a hemolysis depressant wherein $R^1$, $R^2$, and $R^3$ in the general formula (I) are independently an aliphatic hydrocarbon group of 1 to 10 carbon atoms and the total number of the carbon atoms of $R^1$, $R^2$, and $R^3$ is in the range of 10 to 30. This invention further discloses a hemolysis depressant, wherein at least one of the substituents, $R^1$, $R^2$, and $R^3$, in the general formula (I) possesses a branched structure. This invention also discloses a hemolysis depressant wherein the triglyceride compound represented by the general formula (I) is glyceryl tri-2-ethylhexanoate. This invention further discloses a hemolysis depressant which is incorporated in a synthetic resin composition. Further, this invention discloses a hemolysis depressant which is directly added to an erythrocyte-containing solution. This invention also discloses a hemolysis depressant agent which is added in the form of emulsion to the erythrocyte-containing solution.

The various objects described above are further accomplished by a flexible vinyl chloride type resin composition for use in medical appliances, which is characterized by comprising a vinyl chloride type resin, a plasticizer, and a hemolysis depressant comprising a triglyceride compound represented by the general formula (I):

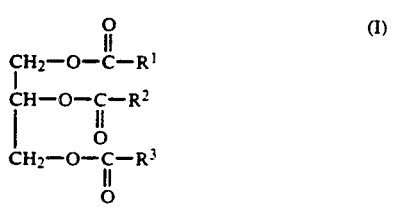

wherein $R^1$, $R^2$, and $R^3$ are independently an aliphatic hydrocarbon group of 1 to 20 carbon atoms and the total number of the carbon atoms of $R^1$, $R^2$, and $R^3$ is in the range of 10 to 36.

This invention further discloses a flexible vinyl chloride type resin composition for medical appliances, which incorporates therein 10 to 45% by weight of a plasticizer and 1 to 20% by weight of triglyceride compound represented by the general formula (I). This invention also discloses a flexible vinyl chloride type resin composition for medical appliances, which incorporates therein 3 to 10% by weight of a triglyceride compound represented by the general formula (I). Further, this invention discloses a flexible vinyl chloride type resin composition for medical appliances, wherein the plasticizer incorporated therein possesses a low exuding property. This invention also discloses a flexible vinyl chloride type resin composition for medical appliances, wherein the plasticizer incorporated threrein is selected from the group consisting of trialkyl trimellitates, di-normal alkyl phthalates, and tetraalkyl pyromellitates. This invention further discloses a flexible vinyl chloride type resin composition for medical appliances, wherein the plasticizer incorporated therein is di-normal decyl phthalate. This invention also discloses a flexible vinyl chloride resin type composition for medical appliances, wherein the plasticizer incorporated therein is trioctyl trimellitate.

The various objects described above are further accomplished by a flexible resin composition for medical appliances, which is characterized by incorporating in a flexible resin composition containing no plasticizer a hemolysis depressant comprising a triglyceride compound represented by the general formula (I):

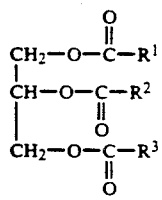

(I)

wherein $R^1$, $R^2$ and $R^3$ are independently an aliphatic hydrocarbon group of 1 to 20 carbon atoms and the total number of the carbon atoms of $R^1$, $R^2$, and $R^3$ is in the range of 10 to 36.

This invention further discloses a flexible resin composition for medical appliances, wherein the triglyceride compound represented by the general formula (I) is incorporated in a proportion falling in the range of 5 to 35% by weight. This invention also discloses a flexible resin composition for medical appliances, wherein the flexible resin is an internally plasticized vinyl chloride type resin, a polyester, a polyurethane, an ethylene-vinyl acetate copolymer, or a polymer blend of polyvinyl chloride with an ethylene-vinyl acetate copolymer or polyvinyl chloride with a polyurethane- or ethylene-type polymer This invention further discloses a flexible resin composition for medical appliances, wherein the internally plasticized vinyl chloride type resin incorporated therein is a urethane-vinyl chloride copolymer, a vinyl acetate-vinyl chloride copolymer.

The various objects described above are further accomplished by a rigid resin composition for medical appliances, which is characterized by having incorporated in a rigid resin composition a hemolysis depressant comprising a triglyceride compound represented by the general formula (I):

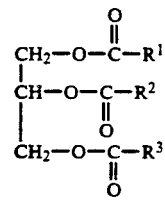

(I)

wherein $R^1$, $R^2$, and $R^3$ are independently an aliphatic hydrocarbon group of 1 to 20 carbon atoms and the total number of the carbon atoms of $R^1$, $R^2$, and $R^3$ is in the range of 10 to 36.

This invention further discloses a rigid resin composition for medical appliances, wherein the triglyceride compound represented by the general formula (I) is incorporated therein in a proportion falling in the range of 0.5 to 5% by weight. This invention also discloses a rigid resin composition for medical appliances, wherein the rigid resin incorporated therein is selected from the group consisting of acryl type resins, styrene type resins, olefin type resins, thermoplastic polyester type resins, and polycarbonates. Further, this invention discloses a rigid resin composition for medical appliances, wherein the acrylic type resin is a homopolymer or copolymer of methyl methacrylate, methyl acrylate, ethyl methacrylate, ethyl acrylate, acrylonitrile, or methacrylonitrile. This invention also discloses a rigid resin composition for medical appliances, wherein the styrene type resin is polystyrene, an acrylonitrilre-syrene copolymer, or an acrylonitrile-butadiene-styrene copolymer. This invention further discloses a rigid resin composition for medical appliances, wherein the olefin type resin is polyethylene, polypropylene, or an ethylene-propylene copolymer. This invention also discloses a rigid resin composition for medical appliances, wherein the thermoplastic polyester resin is polyethylene terephthalate or polybutylene terephthalate.

The various objects described above are also accompliḧsed by a medical implement, which is characterized by being substantially formed with a flexible vinyl chloride type resin composition comprising a vinyl chloride type resin, a plasticizer, and a hemolysis depressant comprising a triglyceride compound represented by the general formula (I):

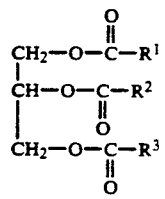

(I)

wherein $R^1$, $R^2$, and $R^3$ are independently an aliphatio hydrocarbon 9group of 1 to 20 carbon atoms and the total number of the carbon atoms of $R^1$, $R^2$, and $R^3$ is in the range of 10 to 36.

This invention further discloses a medical implement which is container for storing blood. This invention also discloses a medical implement which is capable of withstanding sterilization in an autoclave.

The various objects described above are further accomplished by a medical implement, which is characterized by being substantially formed with a flexible resin composition having incorporated in a flexible resin composition containing no plasticizer a hemolysis depressant comprising a triglyceride compound represented by the general formula (I):

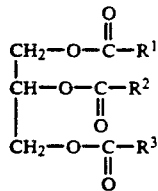

wherein $R^1$, $R^2$, and $R^3$ are independently an aliphatic hydrocarbon group of 1 to 20 carbon atoms and the total number of the carbon atoms of $R^1$, $R^2$, and $R^3$ is in the range of 10 to 36.

This invention further discloses a medical implement which is a blood collection tube. This invention also discloses a medical implement which is capable of withstanding sterilization in an autoclave.

The various objects described above are accomplished also by a medical implement, which is characterized by being substantially formed with a rigid resin composition incorporating in a rigid resin composition a hemolysis depressant comprising a triglyceride compound represented by the general formula (I):

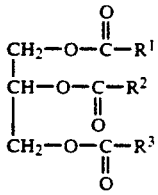

wherein $R^1$, $R^2$, and $R^3$ are independently analiphatic hydrocarbon group of 1 to 20 carbon atoms and the total number of the carbon atoms of $R^1$, $R^2$, and $R^3$ is in the range of 10 to 36.

This invention further discloses a medical implement which is a blood collection tube.

The various objects described above are also accomplished by a blood preserving liquid composition, which is characterized by incorporating therein a hemolysis depressant comprising a triglyceride compound represented by the general formula (I):

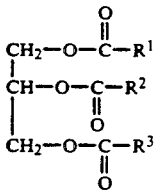

wherein $R^1$, $R^2$, and $R^3$ are independently an aliphatic hydrocarbon group of 1 to 20 carbon atoms and the total number of the carbon atoms of $R^1$, $R^2$, and $R^3$ is in the range of 10 to 36 and other blood preservative component.

This invention further discloses a bloodpreserving liquid composition, wherein the blood preserving liquid is an anticoagulant preserving liquid. This invention also discloses a blood preserbing liquid composition, wherein the other blood preservative component is at least one compound selected from the group consisting of sodium citrate, citric acid, grape sugar, monosodium phosphate, adenine, sodium chloride, mannitol, maltose, multitol, sorbitol, sucrose, and lactose. This invention further discloses a blood preserving liquid composition, wherein the triglyceride compound represented by the general formula (I) is incorporated in a substratal liquid selected from the group consisting of ACD solution, CPD, solution, CPDA-1 solution, CPDA-2 solution, SAG solution, and an SAG solution incorporating therein mannitol, maltose, multitol, sorbitol, sucrose or lactose. This invention also discloses a blood preserving liquid composition, wherein the triglyceride compound represented by the general formula (I) is incorporated therein in a final concentration falling in the range of $10\mu M$ to 10mM. Further, this invention discloses a blood preserving liquid composition, wherein the triglyceride compound represented by the general formula (I) is incorporated therein in a final concentration falling in the range of $30\mu M$ to 5mM.

The various objects described above are further accomplished by a plasticizer for vinyl chloride type resins, which comprises a triglyceride compound represented by the general formula (I'):

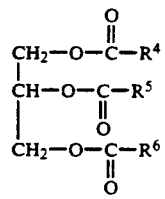

where $R^4$, $R^5$, and $R^6$ are independently an aliphatic hydrocarbon group of 1 to 11 carbon atoms.

This invention further discloses a plasticizer for vinyl chloride type resins, where $R^4$, $R^5$, and $R^6$ in the general formula (I') are independently an aliphatic hydrocarbon group of 5 to 9 carbon atoms. This invention also discloses a plasticizer for vinyl chloride type resins wherein at least one of the substituents, $R^4$, $R^5$, and $R^6$, in the general formula (I') possesses a branched structure. Further, this invention discloses a plasticizer for vinyl chloride type resins, wherein the triglyceride compound is glyceryl tri-2-ethylhexanoate. This invention also discloses a plasticizer for vinyl chloride type resins, wherein the palsticizer is incorporated in a proportion falling in the range of 5 to 40% by weight.

The various objects described above are further accomplished by a vinyl chloride type resin composition for medical appliances, which is characterized by having incorporated in a vinyl chloride type resin a plasticizer comprising a triglyceride compound represented by the general formula (I'):

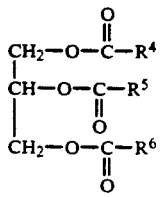

wherein $R^4$, $R^5$, and $R^6$ are independently an aliphatic hydrocarbon group of 1 to 11 carbon atoms.

This invention further discloses a vinyl chloride type resin composition for medical appliances, wherein the triglyceride represented by the general formula (I') is incorporated in a proportion falling in the range of 5 to 40% by weight. This invention also discloses a vinyl chloride type resin composition for medical appliances, wherein 5 to 60 parts by weight of the triglyceride compound represented by the general formula (I'), 2 to 8% by weight of an epoxidized vegetable oil, and 0.03 to 2% by weight of a stabilizer are incorporated.

The various objects described above are further accomplished by a medical implement, which is characterized by being substantially formed with a vinyl chloride type resin composition having incorporated in a vinyl chloride type resin a plasticizer comprising a triglyceride compound represented by the general formula (I');

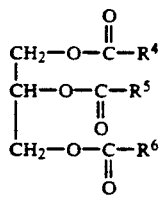
(I')

wherein $R^4$, $R^5$, and $R^6$ are independently an aliphatic hydrocarbon group of 1 to 11 carbon atoms.

This invention also discloses a medical implement, which is capable of withstanding sterilization in an autoclave. This invention further discloses a medical implement which is a container for storing blood.

BRIEF DESCRIPTION OF THE DRAWING

FIG. 2 is a cross section illustrating a blood collection tube as a typical implement formed substantially of a rigid resin composition for medical appliances incorporating therein a hemolysis implement as another embodiment of the present invention.

FIGS. 3 and 4 are cross sections illustrating the conditions in which the embodiments mentioned above are put to use.

BEST MODE FOR CARRYING OUT THE INVENTION

Figure 1:
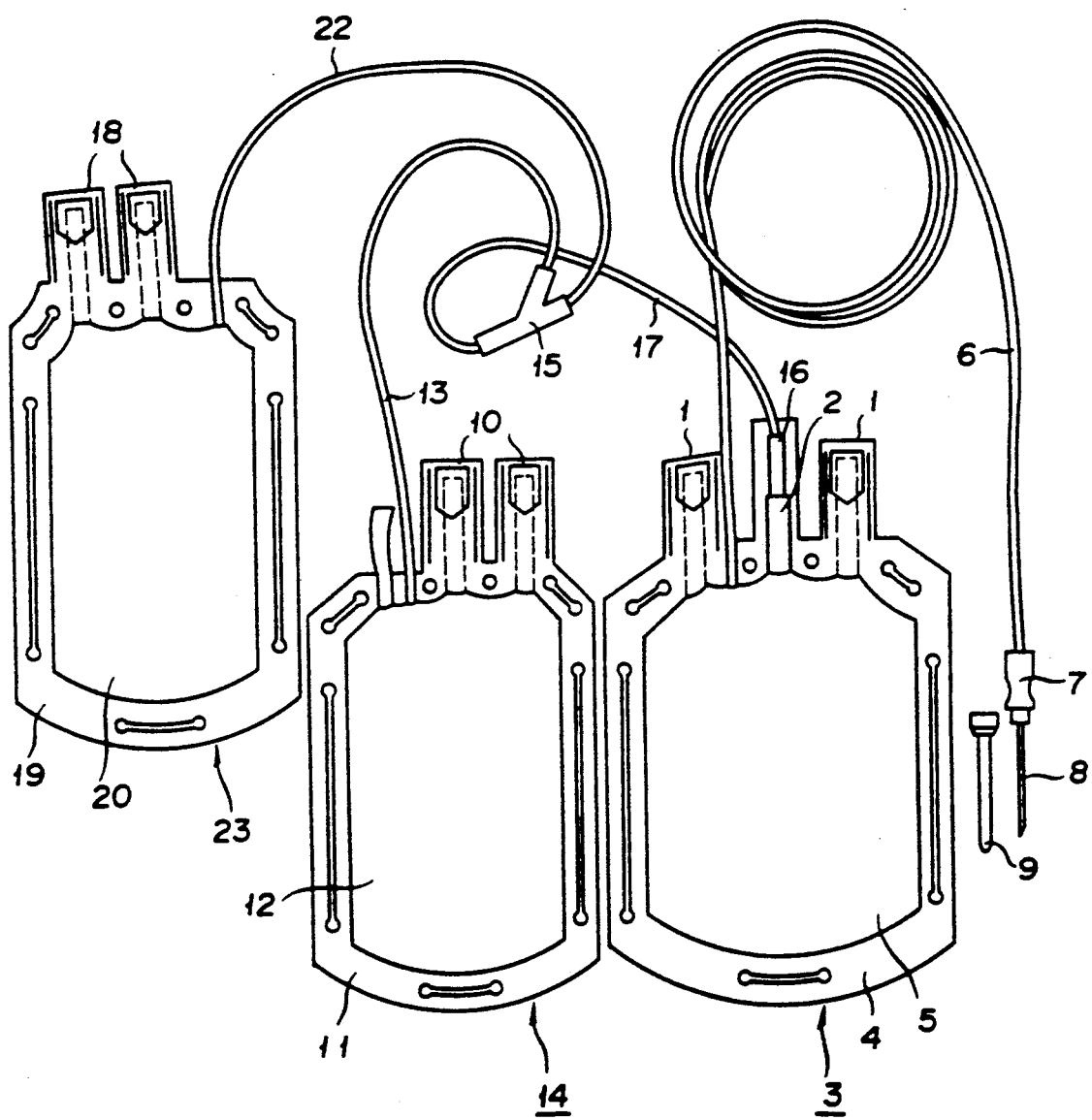
FIG. 1 is a front view illustrating a blood bag as a typical medical implement formed substantially of a flexible resin composition for medical appliances incorporating therein a hemolysis implement as one embodiment of the present invention.

The hemolysis depressant of the present invention comprises a triglyceride compound which is represented by the general formula (I):

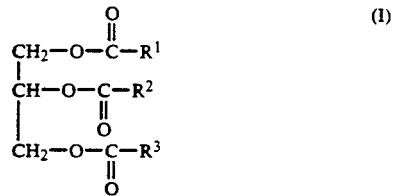
(I)

wherein $R^1$, $R^2$, and $R^3$ are independently an aliphatic hydrocarbon group of 1 to 20 carbon atoms and the total number of the carbon atoms of $R^1$, $R^2$, and $R^3$ is in the range of 10 to 36.

Glycerine esters of medium chain-length fatty acids like triglyceride compounds represented by the general formula (I) are compounds of such great safety as have been heretofore used as oily agents for cosmetic articles and medicines. As concerns the toxicity of these glycerine esters of medium chain-length fatty acids as used in an independent from, the $LD_{50}$ (lethal dose 50) of glycerine tricaprylate, for example administered intravenously to mice is 3,700 mg/kg [Acta Physiol. Scan., 40, 338 (1987)], whereas the $LD_{50}$ of di-2-ethylhexyl phthalate similarly administered is 1,600 mg/kg [National Technical Information Service PB 250,102]. In the reproduction test using rats, the $TD_{LO}$ (toxic dose) of glyceryl tricaprylate administered orally is 250 g/kg [Studies in Medical Products, 4, 180 (1973)], whereas the $TD_{LO}$ of di-2-ethylhexyl phthalate is reported to be 7,140 mg/kg [Toxicol. Appl. Pham.,36,253 (1973)]. From these data, it is clear that the triglyceride compounds represented by the general formula (I) are safe substances because of low toxicity. It is surprising to note that the triglyceride compounds represented by the general formula (I) are capable of exhibiting an antihemolytic activity on erythrocytes similarly to di-2-ethylhexyl phthalate and, unlike di-2-ethylhexyl phthalate, are not recognized to manifest any activity in curbing the phenomenon of aggregation of blood platelets.

Further, the triglyceride compounds represented by the general formula (I) are invariably capable of being dispersed in erythrocyte-containing liquids and are capable of being uniformly dispersed therein particularly when they are in the form of emulsions. Thus, they can be added directly to such erythrocyte-containing liquids. Since these compounds possess thorough compatibility with various synthetic resins represented by vinyl chloride type resins, they are enabled to function as a hemolysis depressant when they are incorporated in synthetic resin compositions. For example, when a synthetic resin composition incorporating therein a triglyceride compounds represented by general formula (I) is exposed to contact with an erythrocyte-containing liquid, the compounds exude from the resin composition and pass into the erythrocyte-containing liquid and, therefore, bring about the same effect as when they are directly added to the erythrocyte-containing liquid.

Further, in the embodiment which resides in incorporating the triglyceride compounds represented by general formula (I) in a flexible vinyl chloride type resin composition, the effect to be brought about by this embodiment can be further enhanced by additionally incorporating therein a plasticizer other than di-2-ethylhexyl phthalate, particularly a plasticizer of the foregoing description which possesses high safety and a low exuding property. To be more specific, when the aforementioned flexible vinyl chloride type resin composition is exposed to contact with blood, the hemolysis of erythrocytes is prevented by the action of triglyceride compounds represented by general formula (I) exuding from the resin composition and passing into the blood and, in the meantime, the resin composition does not liberate through exudation any substance which inhibits platelets aggregation similarly to di-2-ethylhexyl phthalate. This resin composition, therefore, excels in physiological safety and in the ability to protect erythrocytes. The same thing applies to the embodiment which resides in incorporating the triglyceride compound represented by general formula (I) in a flexible resin composition containing no plasticizer. (This is because the problem essentially due to the exudation of a plasticizer cannot arise in the present embodiment.) For this reason, the flexible vinyl chloride type resin composition for medical use and the flexible resin composition for medical use contemplated by the present invention are suitable as materials for medical implements. Further, the shaped articles formed by using these materials, owing to the excellence thereof in safety, fabricability, flexibility, transparency, and thermal resistance, are enabled to manifest the effect thereof to the fullest extent when the shaped articles are used as medical implements. The effect is prominent particularly when the shaped articles are medical implements such as the blood bag destined to contact body fluids such as blood.

Similarly, in the embodiment which resides in incorporating the triglyceride compound represented by the general formula (I) in a rigid resin composition, triglyceride compound represented by the general formula (I) functions to prevent the hemolysis of erythrocytes and offers highly satisfactory protection for erythrocytes. The resin composition, therefore, is suitable as a material for medical implements. The shaped articles formed by using this material, owing to their excellence in safety, fabricability, transparency, and thermal resistance, are enabled to manifest the effect to the fullest extent when the shaped articles are used as medical implements. The effect is prominent particularly when the shaped articles are medical implements such as the blood collection tubes which are destined to contact body fluids such as blood.

The aforementioned triglyceride compound represented by the general formula (I) is capable of being dispersed in the form of emulsion or clathrate compound in an aqueous solution. Further, it exhibits the aforementioned ability to prevent the hemolysis of erythrocytes even when it is in the form mentioned above. When it is incorporated in a blood preserving liquid with the aid of a suitable surfactant which is incapable of exerting any adverse effect upon blood components or an α-cyclodextrin, the produced blood preserving liquid excels in the ability to protect erythrocytes as well as in physiological safety. When the blood preserving liquid of this invention is added to an erythrocyte-containing liquid such as whole blood or concentrated red cells, for example, most of the erythrocytes can be retained for a long time in the same state as immediately after blood extraction. Thus, the problem arising in the transfusion of preserved blood can be eliminated.

The plasticizer of the present invention is a triglyceride compound represented by the general formula (I'):

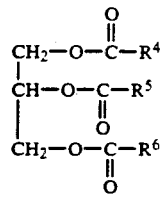

wherein $R^4$, $R^5$, and $R^6$ are independently an aliphatic hydrocarbon group of 1 to 11, preferably 5 to 9 carbon atoms.

Such glycerine esters of medium chain-length fatty acid as triglyceride compounds represented by the general formula (I') are safe substances of low toxicity as compared with di-2-ethylhexyl phthalate heretofore used as a plasticizer. It is surprising to note that the triglyceride compounds represented by the general formula (I') excel in compativility with vinyl chloride type resins and manifest ample plasticizing efficiency therefor.

The vinyl chloride type resin composition of the present invention which incorporates a triglyceride compound represented by the general formula (I') as a plasticizer, therefore, proves to be a material suitable for medical implements. The shaped articles obtained by molding this material are excellent in safety, processibility, flexibility, transparency, and resistance to heat. When these shaped articles are used as medical implements, they can manifest their inherent effects to the fullest extent. These effects are particularly conspicuous when these medical implements are destined to contact blood or body fluid.

Now, the present invention will be described more specifically below with reference to working examples. To facilitate comprehension of this invention, the paragraphs titled "Hemolysis Depressant," "Resin Composition for Medical Appliances Incorporating the Hemolysis Depressant," "Medical Implement Incorporating the Hemolysis Depressant," "Blood Preserving Liquid Incorporating the Hemolysis Depressant," "Plasticizer," "Medical Implement Formed with Vinyl Chloride Type Resin composition for Medical Appliances Incorporating the Palsticizer," and "Example," will be covered in the following part of the test.

Hemolysis Depressant

The Hemolysis Depressant of the present invention comprises a triglyceride compound represented by the general formula (I):

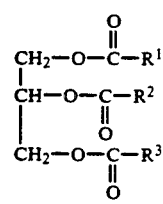

wherein $R^1$, $R^2$, and $R^3$ are independently an aliphatic hydrocarbon group of 1 to 20, more desirably 1 to 14, and most desirably 6 to 10, carbon atoms and the total number of the carbon atoms of $R^1$, $R^2$, and $R^3$ is in the range of 10 to 36, more desirably 10 to 30, and most desirably 10 to 24.

In the general formula (I) representing the triglyceride compounds of this invention, the total number of the carbon atoms in $R^1$, $R^2$, and $R^3$ is limited to the range of 1 to 20 for the following reason. If the total number of the carbon atoms exceeds 20, the triglyceride compound assumes a solid state in the range of temperatures at which whole blood or an erythrocyte-containing solution such as a red cell concentrate is stored, and, therefore, is not smoothly dispersed easily in the erythrocyte-containing solution and cannot be expected to manifest an antihemolytic action sufficiently. When the triglyceride compound is used in the form incorporated in a varying synthetic resin composition, it has a possibility of losing compatibility with the resin composition. This adverse effect is also produced when the total number of the carbon atoms in $R^1$, $R^2$, and $R^3$ exceeds 36. If the total number of the carbon atoms in $R^1$, $R^2$, and $R^3$ is less than 10, the triglyceride compound has a possibility of inducing hemolysis. Then, in the general formula (I) representing the triglyceride compounds of this invention, at least one of the substituents, $R^1$, $R^2$, and $R^3$, is desired to possess a branched structure even from the standpoint of enhancing the antihemolytic effect of the triglyceride compound. For the triglyceride compound represented by the general formula (I), all the aliphatic hydrocarbon groups, $R^1$, $R^2$, and $R^3$ are not required to be identical with one another. They may be a combination of aliphatic hydrocarbn groups differing in chain length from one another. Further, the aliphatic hydrocarbon groups, $R^1$, $R^2$, and $R^3$, may be saturated aliphatic hydrocarbon groups or unsaturated aliphatic hydrocarbon groups, To concrete, the triglyceride compound represented by the general formula (IO are glyceryl trivalerate (trivalerin), glyceryl triisovalerate, glyceryl tricaproate, glyceryl tricaprylate, glyceryl tri-2-ethylhexanoate, glyceryl trilaurate (trilaurin), butyryl divaleryl glycerin, butyryl diisovaleryl glycerin, valeryl dihexanoyl glycerin, hexanoyl dioctanoyl glycerin, hexanoyl bis-(2-ethylhexanoyl)glycerin, octanoyl bis-(2-ethylhexanoyl)glycerin, dioctanoyl 2-ethylhexanoyl glycerin, 2-ethylhexanoyl didecanoyl glycerin, bis(2-ethylhexanoyl) decanoyl glycerin, decanoyl dilauroyl glycerin, and dilauroyl millistoyl glycerin. Among other triglyceride compounds enumerated above, glyceryl tri-2-ethylhexanoate and octanoyl bis-(2-ethylhexanoyl)glycerin prove to be particularly desirable. The best all the triglyceride compounds is glyceryl tri-2-ethylhexanoate.

The hemolysis depressant of the present invention comprising triglyceride compound represented by the general formula (I) can be used as directly added to the erythrocyte-containing liquid such as whole blood or concentrated red cells (inclusive of the case wherein the addition is made to an erythrocyte-containing liquid contained in advance in a blood container such as the blood bag in combination with an anticoagulant preservative liquid such as ACD (acid-citrate dextrose) or CPD (citrate phosphate dextrose) or it can be used as incorporated in a synthetic resin composition for medical use to form blood containers such as the blood bag and the blood collection tube and medical implements such as the catheter, transfusion set, and blood circuits which are destined to contact an erythrocyte-containing liquid.

In the direct addition of the hemolysis depressant of this invention comprising the triglyceride compound represented by the general formula (I) to the erythrocyte-containing liquid, while the compounds to be described in detail later on may be added in their unmodified form, they are added more desirably in the form of emulsion or clathrate compound so as to be uniformly dispersed and mixed in the erythrocyte-containing liquid. The preparation of the emulsion of the triglyceride compound represented by the general formula (I) can be attained by dispersing the triglyceride compound in a suitable aqueous medium such as a saline water or buffer or in an anticoagulant preservative such as ACD liquid or CPD liquid with the aid of a surfactant or curing castor oil which has no adverse effect upon blood components as illustrated below. The preparation of the clathrate compound of the triglyceride compound represented by the general formula (I) is attained by the use of a α-cyclodextrin, for example. The amount of the hemolysis depressant to be added directly to the erythrocyte-containing liquid, though variable with the kind of the erythrocyte-containing liquid and the kind of the triglyceride compound represented by the general formula (I), falls in the range of $10\mu M$ to 10mM, preferably $30\mu M$ to 5mM, as final concentration based on the amount of whole blood.

In the incorporation of the hemolysis depressant of the present invention comprising the triglyceride compound represented by the general formula (I) in a synthetic resin composition for medical use, since the triglyceride compound represented by the general formula (I) can be uniformly dispersed and mixed in various resin compositions such as, for example, vinyl chloride type resins, olefin type resins, styrene type resins, (meth)acryl type resins, and carbonate type resin, it suffices to add the triglyceride compound to the synthetic resin composition while the resin composition is being blended. The synthetic resin composition which has incorporated the triglyceride compound as described above can be formed in a given shape by any of the conventional molding methods such as, for example, calender molding, extrusion molding, injection molding, and plastisol molding. The adhesion of the resin composition to a surface can be attained by any of the conventional methods such as, for example, high frequency welding, thermal welding and supersonic welding. When the triglyceride compound represented by the general formula (I) is incorporated in one of such various resin composition, the triglyceride compound which exudes from the synthetic resin composition and comes into contact with the erythrocyte-containing liquid to manifest the action to protect erythrocytes. The amount of the hemolysis depressant comprising the triglyceride compound represented by the general formula (I) to be incorporated in the synthetic resin composition, though variable with the kind of the synthetic resin composition used to incorporate the hemolysis depressant and the kind of the triglyceride compound, is generally in the range of 1 to 20% by weight, preferably 3 to 10% by weight based on the amount of the resin composition. So long as the amount of the triglyceride compound so incorporated falls in the aforementioned range, it brings about the action to protect erythrocytes effectively when the erythrocyte-containing liquid is brought into contact with the medical implement to be formed with the aforementioned synthetic resin composition. The hemolysis depressant so incorporated does not substantially impair the physical properties of the synthetic resin composition.

Resin Composition for Medical Appliances Incorporating the Hemolysis depressant The resin composition contemplated for medical use by the present invention is obtained by incorporating in a varying synthetic resin composition the hemolysis depressant comprising the triglyceride compound represented by the general formula (I) described above.

As described above, the triglyceride compound represented by the general formula (I) possess compatibility with various synthetic resins and can be uniformly dispersed in various flexible and rigid synthetic resin compositions. A triglyceride compound represented by the general formula (I) incorporated in a resin composition for medical use is in such quality that, when the synthetic resin composition comes into contact with an erythrocyte-containing liquid, the compound exudes from the resin composition and passes into the liquid and acts to protect the erythrocytes. The resin composition for medical use according to this invention, therefore, is most suitable as a material for medical implements such as the blood bag and the blood collection tube which are destined to contact blood. The resin composition for medical use may be prepared as flexible products or rigid products, depending on purposes for which the products are adopted. In various resin composition, flexible vinyl chloride type resin compositions may be cited as most desirable. When the triglyceride compound represented by general formula (I) is incorporated in a flexible vinyl chloride type resin composition, the inhibition of hemolysis in a erythrocyte-containing liquid is effected by the compound which exudes from the resin composition and passes into the liquid. Thus, the resin composition is allowed to use a plasticizer other than di-2-ethylhexyl phthalate, particularly a plasticizer of the description which exhibits high physiological safety and a low exuding property.

Flexible vinyl chloride type resin composition for medical use

The flexible vinyl chloride type resin composition for medical use according to this invention is characterized by a composition which comprises a vinyl chloride type resin, a plasticizer, and a hemolysis depressant comprising the triglyceride compound represented by the general formula (I).

As the vinyl chloride resin to be used in the flexible vinyl chloride type resin composition contemplated by this invention for medical use, there can be used vinyl chloride homopolymer, polyvinylidene chloride, or a varying copolymer containing not less than 40% by weight, more desirably not less than 65% by weight, and most desirably not less than 75% by weight, of vinyl chloride in addition to the balance of other copolymerizable monomer. The average polymerization degree of the vinyl chloride resin is in the range of 400 to 3,000, more desirably 600 to 2,700, and most desirably 800 to 1,700. Examples of the comonomer for vinyl chloride in the copolymer include vinylidene chloride, ethylene, propylene, vinyl acetate, vinyl bromide, vinyl fluoride, styrene, vinyl toluene, vinyl pyridine, acrylic acid, alkyl acrylate (such as methyl acrylate, ethyl acrylate, isopropyl acrylate, n-butyl acrylate, and 2-ethylhexyl acrylate), methacrylic acid, alkyl methacrylates (such as methyl methacrylate, ethyl methacrylate, and 2-ethylhexyl methacrylate), acrylonitrile, and methacrylonitrile. Optionally the vinyl chloride may incorporate therein styrene-acrylonitrile copolymer or styrene-methacrylonitrile copolymer.

The plasticizer to be used in the flexible vinyl chloride type resin composition contemplated for medical use by the present invention is desired to possess high physiological safety and preferably exhibit a low exuding property. As examples of the plasticizer meeting this description, there can be cited dinormal alkyl phthalates such as dinormal octyl phthalate, dinormal nonyl phthalate, dinormal decyl phthalate, dinormal undecyl phthalate, and dilauryl phthalate, trialkyl trimellitates such as tri-2-ethylhexyl trimellitate and tri-normal octyl trimetllitate, and tetraalkyl pyromellitates such as tetra-2-ethylhexyl pyromellitate. Among other plasticizers enumerated above, di-normal decyl phthalate and trioctyl trimellitate prove to be particularly desirable. In the flexible vinyl chloride type resin composition for medical use according to the present invention, the plasticizer of the foregoing description is incorporated in an amount generally in the range of 10 to 45% by weight though variable with the kind of the plasticizer to be used. This range is important because the produced resin composition lacks flexibility if the amount of the plasticizer incorporated is less than 10% by weight or because the composition is apt to induce the phenomenon of bleeding if the amount of the plasticizer exceed 45% by weight.

Then, in the flexible vinyl chloride type resin composition for medical appliances according with the present invention, a hemolysis depressant comprising a triglyceride compound represented by the general formula (I) is incorporated. The triglyceride compound represented by the general formula (I) is thus incorporated for the purpose of preventing hemolysis. Since this triglyceride compound exhibits a plasticizing property for vinyl chloride type resins as described fully later on, it fulfils an additional function in enhancing the plasticization of a vinyl chloride type resin with a plasticizer.

In the flexible vinyl chloride type resin composition for medical appliances according with the present invention, the triglyceride compound represented by the general formula (I) is incorporated in a proportion falling in the range of 1 to 20% by weight, preferably 3 to 10% by weight. The proportion is limited to the range mentioned above for the following reason. If the amount of the triglyceride compound represented by the general formula (I) so incorporated in less than 1% by weight, the activity manifested by the added triglyceride compound in curbing the hemolysis of erythrocytes is not sufficient. Conversely, if this amount exceeds 20% by weight, the added triglyceride compound has a possibility of degrading the physical properties of the flexible vinyl chloride type resin composition.

Further, the flexible vinyl chloride type resin composition for medical use according to the present invention, when necessary, may incorporate therein an epoxidized vegetable oil such as epoxidized soy bean oil or epoxidized linseed oil intended as a combination stabilizer and auxiliary plasticizer; a metallic soap of calcium or zinc salt of stearic acid, lauric acid, ricinoleic acid, or naphthenic acid intended as a stabilizer; a lubricant; an antioxidant; etc. The amount of the epoxidized vegetable oil to be additionally incorporated as a combination stabilizer and auxiliary plasticizer is in the range of 3 to 10% by weight, preferably 6 to 9% by weight and the amount of the metallic soap to be incorporated as a stabilizer is in the range of 0.05 to 3% by weight, preferably 0.1 to 1.5% by weight.

When the vinyl chloride type resin composition for medical use according to the present invention is to be formed in a desired shape, this formation can be accomplished by any of the conventional methods such as, for example, calender molding, extrusion molding, and plastisol molding methods. When the resin composition is to be joined to a surface, the adhension can be effected by high frequency welding, thermal welding, or supersonic welding, etc.

Flexible Resin Composition for Medical Use

The hemolysis depressant of the present invention can be incorporated as effectively in any flexible resin composition than the flexible vinyl chloride resin composition as in the vinyl chloride resin composition, to give rise to a highly desirably flexible resin composition for medical use.

The flexible resin composition contemplated for medical use by the present invention, therefore, is characterized by incorporating the hemolysis depressant comprising the triglyceride compound represented by general formula (I) described above into said flexible resin composition containing no plasticizer.

The flexible resin to be used in the manufacture of the flexible resin composition for medical use is a flexible resin which exhibits sufficient plasticity, particularly flexibility, without being externally plasticized with a plasticizer (providing that the term "plasticizer" as used in the present specification refers, unless otherwise defined particularly, to an external plasticizer in the narrow sense of the word). The flexible resin composition for medical use, therefore, contains no plasticizer. This means that this flexible resin composition for medical use is inherently incapable of entailing as a problem the disadvantage that a plasticizer exudes from the resin composition and exerts an adverse effect on blood components or on the vital system.

As examples of the flexible resin of the foregoing description, there can be cited internally plasticized vinyl chloride type resins, polyethylene, thermoplastic polyester, polyurethane, ethylene-vinyl acetate copolymer, and polymer blends of polyvinyl chloride with polyurethane, ethylene type polymers (such as, for example, a product marketed under trademark designation of "ELVALOY"), or caprolactone type polymers. Of course, these are not exclusive examples. Examples of the internally plasticized vinyl chloride resin include urethane-vinyl chloride copolymer, vinyl acetate-vinyl chloride copolymer, and ethylene-vinyl acetate-vinyl chloride copolymer. In the internally plasticized vinyl chloride type resin of this nature, the gravimetric ratio of the vinyl chloride monomer component to the monomer component bestowed with a plasticizing capacity and used for copolymerization falls in the range of about 7:3 to 3:7, preferably 6:4 to 4:6. The polyethylene for use in the copolymerization is desired to be a low-density polyethylene preferably possessing a melt index in the range of about 0.1 to 5. The thermoplastic polyester for the copolymerization is typified by a polyethylene terephthalate film. Typical examples of the polyurethane include polyester type polyurethane and polyether type polyurethane elastomers. Preferably, the polyurethane is a polyether type segmented polyurethane. In the ethylene-vinyl acetate copolymer, the gravimetric ratio of the ethylene monomer component to the vinyl acetate component is approximately in the range of 95:5 to 70:30, preferably 90:10 to 80:20.

This invention does not discriminate the flexible resin composition for medical use particularly on account of the kind of flexible resin component. Among other various available flexible resin components, polyurethane and ethylene-vinyl acetate copolymer can be cited as particularly desirable flexible resins components.

In the flexible resin composition of this invention for medical use, the aforementioned hemolysis depressant comprising the triglyceride compound represented by the general formula (I) is incorporated. The hemolysis depressant is incorporated in the flexible resin composition contemplated for medical use by this invention in a concentration in the range of 5 to 35% by weight, preferably 10 to 25% by weight. This range is important because the produced composition manifests no sufficient action to inhibit hemolysis of erythrocytes if the concentration is less than 5% by weight or because the incorporated hemolysis depressant possibly impair the physical properties of the flexible resin composition if the concentration exceeds 35% by weight.

Optionally, the flexible resin composition of this invention for medical use may incorpoate therein such additives as stabilizer, lubricant, and antioxidant.

When the flexible resin composition of this invention for medical use is to be formed in a given shape, this formation can be effected by any of the various conventional methods available for any flexible resin composition, such as calender molding, extrusion molding, blow molding, and plastisol molding. When the flexible resin composition is to be joined to a surface, the adhesion can be effected by high frequency welding, thermal welding, or supersonic welding, etc., depending on the kind of the flexible resin.

Rigid Resin Composition for Medical Use

The rigid resin composition of the present invention for medical use is characterized by incorporating the aforementioned hemolysis depressant comprising the triglyceride compound represented by the general formula (I) into said rigid resin composition.

No particular limits are imposed on the rigid resin to be used in the rigid resin composition contemplated for medical use by this invention, except for the sole requirement that this rigid resin should be physiologically safe and properly compatible with the triglyceride compound represented by the general formula (I). As examples of the rigid resin answering the description, there can be cited acrylic type resins, styrene type resins, olefinic type resins, thermoplastic polyester type resins, and polycarbonate. The rigid resin described above is desired, without reference to the kind thereof, to possess a melt flow index falling in the range of 0.5 to 30 g/10 min., preferably falling in the range of 5 to 12 g/10 min. Examples of the acrylic type resin include homopolymers and copolymers of alkyl (meth)acrylates such as methyl methacrylate, methyl acrylate, ethyl methacrylate, and ethyl acrylate, acrylonitrile, and methacrylonitrile. Examples of the polystyrene type resin include polystyrene, acrylonitrile-styrene copolymer, and acrylonitrile-butadiene-styrene copolymer (ABS resin). Examples of the olefinic type resin include medium- to high-density polyethylenes, polypropylene, and copolymers by the combination of ethylene, propylene, and other $\alpha$-olefins such as ethylene-propylene copolymer. Examples of the thermoplastic polyester type resin are polyethylene terephthalate and polybutylene terephthalate. Examples of the polycarbonate include bisphenol-A type polycarbonate and polycarbonates possessing various carbonate ester type structures. Of course, the rigid resin to be used in the rigid resin composition contemplated for medical use by this invention is not limited to those enumerated above as examples. Polymer blends of various resins are also examples of the rigid resin usable herein.

In the rigid resin composition of the present invention for medical use, the aforementioned hemolysis depressant comprising the triglyceride compound represented by the general formula (I) is incorporated. In the rigid resin composition of this invention for medical use, the hemolysis depressant is incorporated in a concentration in the range of 0.5 to 5% by weight, preferably 2 to 3% by weight. This range is important because the produced composition fails to manifest a sufficient action to inhibit hemolysis if the concentration of the hemolysis depressant is less than 0.5% by weight or because the incorporated hemolysis depressant possible impairs the physical properties of the rigid resin composition if the concentration exceeds 5% by weight.

Optionally, the rigid resin composition of the present invention for medical use may incorporate therein additives such as stabilizer, lubricant, and antioxidant.

When the rigid resin composition of this invention for medical use is to be formed in a given shape, this formation can be effected by any of the conventional methods available for any rigid resin composition such as, for example, injection molding and extrusion molding.

Medical Implement Incorporating the Hemolysis Depressant

The medical implement of the present invention is formed substantially of the flexible vinyl chloride type resin composition for medical use, the flexible resin composition for medical use, or the rigid resin composition for medical use described above.

To be specific, the medical implement of the present invention is characterized by being made substantially of a flexible vinyl chloride type resin composition comprising a vinyl chloride type resin, a plasticizer, and a hemolysis depressant, the triglyceride compound represented by the general formula (I), mention above.

The medical implement is excellent in various properties such as safety, processibility, flexibility, and thermal resistance and particularly in the ability to inhibit hemolysis of erythrocytes.

The medical implement which constitutes another aspect of this invention is characterized by being made substantially of a flexible resin composition incorporating a hemolysis depressant, triglyceride compound represented by the general formula (I), mentioned above into said flexible resin composition containing no plasticizer. This medical implement is excellent in various properties such as safety, processibility, flexibility, and thermal resistance and particularly in the ability to inhibit hemolysis of erythrocytes.

Concrete examples of the medical implement which is made of the flexible vinyl chloride type resin composition for medical use or the flexible resin composition for medical use according to the present invention include blood containers such as blood bag, catheter, transfusion sets, and blood circuits which are destined to contact blood or other body fluids. Containers for packaging such medical implements as mentioned above and containers for prepared agents such as tablets are other examples.

Now, the medical implement of the present invention as embodied in the form of a blood bag will be described below with reference to the accompanying drawing. FIG. 1 illustrates the blood bag. A blood collection bag 3 which is made of the aforementioned flexible vinyl chloride type resin composition or the aforementioned flexible resin composition and provided with a plurality of outlets 1 fitted with peel tab and a connecting outlet 2 has the periphery 4 thereof heat sealed by high frequency heating or some other suitable heating means. This blood collection bag 3 has connected thereto a blood collection tube 6 made of the aforementioned flexible vinyl chloride type resin composition or the aforementioned flexible resin composition and adapted to communicate with an inner space 5 of the blood collection bag 3. A piercing needle 8 is fixed in a needle base 7 formed at the leading end of the blood collection tube 6. This piercing needle 8 is sheathed in a cap 9. To the connecting outlet 2 of the aforementioned blood collection bag 3 is joined a connection tube 17 through the medium of a connection needle 16 formed at the leading end thereof. A connection tube 13 provided with an outlet 10 fitted with a peel tab, made of the aforementioned flexible vinyl chloride type resin composition or the aforementioned flexible resin composition, and adapted to communicate with an inner space 12 of a first satellite bag 14 made of the aforementioned flexible vinyl chloride type resin composition or the aforementioned flexible resin composition and having the periphery thereof similarly heat sealed is caused to communicate with the connection tube 17 via a branched tube 15. Further, a connection tube 22 made of the aforementioned flexible vinyl chloride type resin composition or the aforementioned flexible resin composition and adapted to communicate with an inner space 20 of a second satellite bag 23 provided with an outlet 18 fitted with a peel tab, made of the aforementioned flexible vinyl chloride type resin composition or the aforementioned flexible resin composition, and having the periphery thereof similarly heat sealed is caused to communicate with the connection tubes 17 and 13 via the branched tube 15.

This three-component blood bag is capable of separating collected blood into components in a closed system. From the piercing needle 8 plunged into the vein of a donor, a prescribed amount of blood is drawn into the blood collection bag 3 via the blood collection tube 6. After the extraction of blood is completed, the blood collection bag 3 is subjected to centrifugal force to have the blood separated into an upper layer of platelet rich plasma and a lower layer of hemocytes. Then, the platelet rich plasma of the upper layer is forced out of the blood collection bag 3 and tranferred via the connection tubes 17 and 13 to the first satellite bag 14. The first satellite bag 14 now containing the platelet rich plasma is further subjected to centrifugal force so as to have the platelet rich plasma separated into an upper layer of platelet concentrate and a lower layer of platelet poor plasma. The platelet concentrate of the upper layer is forced out of the first satellite bag 14 and transferred via the connection tubes 13 and 22 into the second satellite bag 23. Even when the collected blood is exposed to contact with the blood bags and the tubes for a long time as by being centrifugally separated into components, distributed into pertinent blood bags and then stored, the aforementioned flexible vinyl chloride type resin composition or the aforementioned flelxible resin composition of which the blood bags and the tubes are made is excellent in the effect of protecting erythrocytes and incapable of interfering with the aggregating ability of platelets and, therefore, permits safe and efficient transfusion of components of blood.

This invention has been so far described as embodied in a blood bag. Other medical implements such as containers for body fluids, catheters, transfusion sets, and blood circuits, containers for packaging the aforementioned medical implements, and containers for prepared agents such as tablets can be similarly advantageously made with the aforementioned flexible vinyl chloride type resin composition or the aforementioned flexible resin composition.

These medical implements by nature are subjected to sterilization prior to use. This sterilization is effected with ethylene oxide or in an autoclave. The sterilization by use of an autoclave is adopted preferably. In the autoclave, the medical implements is sterilized generally at 121° C. for about 60 minutes. The medical implements of the present invention, as described above, possesses ample thermal stability to endure the sterilizing conditions used in the autoclave.

The medical implements which constitutes yet another aspect of this invention is characterized by being made substantially of a rigid resin composition incorporating a hemolysis depressant, triglyceride compound represented by the general formula (I), mentioned above in said rigid resin composition. This medical implement is excellent in various physical properties such as processibility and thermal resistance and particularly in the ability to inhibit hemolysis of erythrocyltes.

Particularly desirable examples of the medical implement of this invention which is made of the aforementioned rigid resin composition for medical use defined above are blood collection tubes which are exposed, particularly for a long time, to contact with body fluids or solutions of body fluid components such as blood or concentrated red cells. Other than these blood collection tubes, desirable examples of the medical implement include blood collection vials, test tubes, petri dishes, and housings for various artificial organs such as artificial lungs and artificial kidneys and heat exchangers. Of course, these are not exclusive examples.

Now, the medical implements of the present invention as embodied in the form of a blood collection tube will be described below with reference to the accompanying drawing. FIG. 2 illustrates a vacuum blood collection tube 31 which comprises a tubular member 32 closed at one end and opened at the other end thereof and made of the rigid resin composition for medical use according to the present invention and a pierceable stopper member 34 made of butyl rubber and adapted to close airtighly an open end 33 of the aforementioned tubular member 32 so as to keep an inner space 35 in a vacuumized state. The vacuum blood collection tube 31 which is constructed as described above is put to use as follows. As illustrated in FIG. 3, the vacuum blood collection tube 31 is inserted, with the aforementioned open end 33 in the lead, into a blood collection tube holder 38 opened at one end and closed at the other end thereof, made of the rigid resin composition for medical use according to the present invention, and provided with a blood collection needle 37 helically fitted into a threaded hole 36 formed in a closed end 40. The blood collection needle 37 is enclosed with a luer elastic sheath member 39 made of rubber and formed of a blood vessel piercing part 37a and a stopper piercing part 37b. When the blood vessel piercing part 37a of the blood collection needle 37 is forcibly inserted into the closed end 40 of the blood collection tube holder 38, the stopper piercing part 37b of the blood collection needle 37 pierces the elastic sheath member 39 and the stopper member 34 and reaches the inner space 35 of the blood collection tube 31 to establish communication between the blood vessel and the aforementioned inner space 35, with the result that the blood inside the blood vessel, owing to the negative pressure in the inner space 35, is caused to flow into the inner space of the blood collection tube 31 in a total amount corresponding to the prevailing degree of vacuum. The extraction of the blood is terminated by removing the blood vessel piercing part 37b of the blood collection needle 37. The blood thus collected is preserved inside the blood collection tube 31 until it is subjected to test. Since the blood collection tube 31 is made of the rigid resin composition for medical use according to this invention as described above, the hemolysis depressant which exudes from the composition and passes into the blood acts to inhibit hemolysis of erythrocytes. Even when the preservation of the blood protracted much in duration, therefore, various measurements made for clinical test are not adversely affected by free hemoglobin. Thus, the measurements are allowed to produce accurate results.

This invention has been so far described as embodied in the form of a blood collection tube. Other medical implements such as blood collection vials, test tuebes, petri dishes, and housings for various artificial organs such as artificial lungs and kidneys and heat exchangers can be made similarly advantageously with the aforementioned rigid resin composition.

Blood Preserving Liquid

The blood preserving liquid of the present invention is characterized by having incorporated therein a hemolysis depressant comprising the triglvceride compound represented by the general formula (I).

The triglyceride compound represented by the general formula (I) is invariably capable of being dispersed in an aqueous solution by the use of a suitable surfactant or α-cyclodestrin which exerts no adverse effect on blood components. Even when it is so dispersed, it still retains the aforementioned ability to inhibit hemolysis of erythrocytes. When a blood preserving liquid incorporates such a compound therein, it is enabled to acquire a notable ability to protect erythrocytes while retaining highly desirable physiological safety. By the addition of the blood preserving liquid to an erythrocyte-containing liquid such as whole blood or concentrated red cells, the greater part of the erythrocytes are allowed to retain for a long time the same state as immediately after extraction of blood. Thus, the problem heretofor encountered in the trasfusion of preserved blood can be eliminated.

Uniform dispersion of the triglyceride compound represented by the general formula (I) in the blood preserving liquid of the present invention can be advantageously accomplished by preparatorily preparing the compound in the form of an emulsion by the use of a surfactant incapable of exerting any adverse effect on blood components or a curing castor oil or in the form of a clathrate compound by the use of α-cyclodextrin, for example. As concrete examples of the surfactant, there can be cited polyoxyethylene sorbitan monoesters (represented by Tween series) such as polyoxyethylene sorbitan monolaurate (Tween 20), polyoxyethylene sorbitan monopalmitate (Tween 40), polyoxyethylene sorbitan monostearate (Tween 60), and polyoxyethylene sorbitan monooleate (Tween 80), polyoxyethylene polyoxypropylene block copolymers (represented by products of BASF marketed under trademark designation of "Pluradot HA-430"), and sorbitan monoacyl esters (represented by Span series) such as sorbitan monoacyl laurate (Span 20), sorbitan monoacyl palmitate (Span 40),sorbitan monoacyl stearate (Span 60), and sorbitan monoacyl oleate (Span 80). Of course, the amount of the surfactant or α-cyclodextrin to be added for this purpose is desired to be on the minimum level tolerable from the standpoint of physiological safety. The triglyceride compound, even when it is added in the form of an emulsion or a clathrate compound, possesses the ability to protect erythrocytes.

The hemolysis depressant comprising the triglyceride compound represented by the general formula (I) behaves in such a manner, though depending on the kind of the hemolysis depressant used, in the blood preserving liquid of the present invention that is produces the ability to protect erythrocytes conspicuously when it is incorporated in the preserved blood in a final concentration in the range of 100μM to 10mM, preferably 30μM to 5mM.

The other components to be contained in the blood preserving liquid of the present invention include the same components as those contained in the conventional blood preserving liquid such as the anticoagulant-preservative which is added to whole blood collected or the conventional blood cell preserving liquid intended for addition to concentrated red cells in the additive system. Concrete examples of these components are sodium citrate, citric acid, glucose, monosodium phosphate, adenine, sodium chloride, mannitol, maltose, sorbitol, multitol, sucrose, and lactose. To be specific, the blood preserving liquid of the present invention is desried to be prepared by using as a basic liquid an anticoagulant preservative liquid such as, for example, ACD solution (acid citrate dextrose anticoagulant solution), CPD solution (citrate phosphate dextrose anticoagulant solution), CPDA-1 solution (citrate phosphate dextrose (1.25 ×CPD) plus 0.25 mM adenine), or CPDA-2 solution (citrate phosphate dextrose (1.75 ×CPD) plus 0.50 mM adenine), or a blood cell preserving liquid such as, for example, SAG solution (saline-adenine-glucose solution), or a modified SAG solution additionally incorporating therein mannitol, maltose, multitol, sorbitol, sucrose, or lactose (Japanese Patent Provisional Publication No. 139,419/81) and incorporating the triglyceride compound represented by the general formula (I) in the basic liquid. Of course, the blood preserving liquid of the present invention is not limited in any sense to the composition mentioned above. It is only required to incorporated the triglyceride compound represented by the general formula (I) and to have a composition safe physiologically.

Actual use of the blood preserving liquid of this invention may be effected by directly adding this liquid o the blood or by placing this liquid in advance in the medical implement such as blood bag and allowing it to be mixed with the blood when the blood is introduced into the implement.

Plasticizer

The plasticizer of the present invention is a triglyceride compound represented by the general formula (I'):

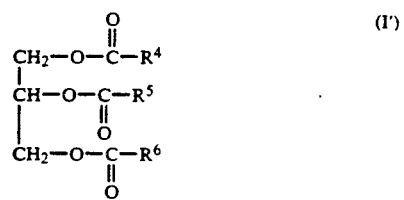

wherein $R^4$, $R^5$, and $R^6$ are independently an aliphatic hydrocarbon group of 1 to 11, preferably 5 to 9, carbon atoms.

In the general formula (I') representing the triglyceride compounds of the present invention, the total number of the carbon atoms in the aliphatic hydrocarbon groups, $R^4$, $R^5$, and $R^6$, is limited to the range of 1 to 11. This is because the triglyceride compound loses its compatibility with the vinyl chloride resin if the total number of the carbon atoms deviates from the range of 1 to 11. When the total number of the carbon atoms in the aliphatic hydrocarbon groups, $R^4$, $R^5$, and $R^6$, is limited to the narrower range of 5 to 9, there ensues a desirable effect that the plasticizing efficiency of the triglyceride compound for the vinyl chloride resin is enhanced. In the triglyceride compound represented by the general formula (I'), it is more desirable from the standpoint of the compatibility with the vinyl chloride resin for the aliphatic hydrocarbon groups, $R^4$, $R^5$, and $R^6$,each to possess a branched structure. In the triglyceride compound represented by the general formula (I'), all the aliphatic hydrocarbon groups, $R^4$, $R^5$, and $R^6$,are not required to be identical with one another. They may be a combination of aliphatic hydrocarbon groups differing in chain length from one another. Further, the aliphatic hydrocarbon groups, $R^4$, $R^5$, and $R^6$,may be either saturated aliphatic hydrocarbon groups or unsaturated aliphatic hydrocarbon groups. To be concrete, the triglyceride compounds represented by the general formula (I') are glyceryl triacetate (triacetin), glyceryl tripropionate (tripropionin), glyceryl tributyrate (tributyrin), glyceryl triisobutyrate (triisobutyrin), glyceryl trivalerate (trivalerin), glyceryl tricaproate, glyceryl trivalerate (trivalerin), glyceryl tricaproate, glyceryl tricaprilate, and glyceryl trilaurate (trilaurin). Among other triglyceride compounds enumerated above, glyceryl tricaproate, glyceryl tricaprilate, glyceryl tri-2-ethylhexanoate, and glyceryl tricaprate prove to be particularly desirable. The best of all these triglyceride compounds is glyceryl tri-2-ethylhexanoate.

The vinyl chloride type resins which can be plasticized by the plasticizer comprising the triglyceride compound represented by the general formula (I') according with the present invention include various vinyl chloride type copolymers described fully later on in addition to the homopolymer of vinyl chloride. The triglyceride compounds represented by the general formula (I') invariably possess ample compatibility and plasticizing efficiency for such vinyl chloride type resins as described above and therefore, can be used each as a plasticizer. In this case, the amount of the triglyceride compound to be incorporated as a placticizer is in the range of 5 to 40% by weight, preferably 10 to 35% by weight. The vinyl chloride type resin compositions which have been plasticized exclusively with a triglyceride compound represented by the general formula (I') according with the present invention possess highly desirable safety. Where this vinyl chloride type resin composition dictates perfect absence of toxicity, it is desired to comprise 5 to 40% by weight of a triglyceride compound represented by the general formula (I'), 2 to 8% by weight of an epoxidized vegetable oil such as epoxidized soybean oil or epoxidized linseed oil as a combination stabilizer and auxiliary plasticizer, and 0.03 to 2% by weight of a metallic soap of calcium or zinc salt of stearic acid, laurylic acid, ricinolic acid, or naphthenic acid as a stabilizer.

The plasticizer of the present invention for vinyl chloride type resins is capable of acting as a plasticizer by itself for vinyl chloride type resins as described above. Optionally, it may be used in combination with other plasticizer.

As such other plasticizer which can be used in combination with the plasticizer of the present invention, any of the conventional plasticizers available for vinyl chloride resins can be used. Examples of the conventional plasticizers useful in this case include phthalic esters such as dibutyl phthalate (DBP), dihexyl phthalate (DHP), di-2-ethylhexyl phthalate (DOP), di-n-octyl phthalate (DnOp), diisooctyl phthalate (DIOP), diheptyl phthalate, didecyl phthalate (DDP), diisodecyl phthalate (DIDP), octyl decyl phthalate, and butyl benzyl phthalate (BBP), trimellitic esters such as tributyl trimellitate and trioctyl trimellitate, aliphatic polybasic esters such as dioctyl adipate (DOA), dioctyl azelate (DOZ), and dioctyl sebacate (DOS), phosphoric esters such as tricresyl phosphate (TCP), trixylenyl phosphate (TXP), monooctyl diphenyl phosphate (Santicizer 141), monobutyl xylenyl phosphate (B-2-X), and trioctyl phosphate (TOF), citric esters such as tributyl acetyl citrate, trioctyl acetyl citrate, and tributyl citrate, and butyl phthalyl butyl glycolate (BPBG).

Vinyl Chloride Type Resin Composition for Medical Appliances Incorporating Plasticizer The flexible vinyl chloride type resin composition for medical appliances according with the present invention is obtained by having incorporated in a vinyl chloride type resin the plasticizer comprising a triglyceride compound represented by the general formula (I'). Since the vinyl chloride type resin composition of the present invention incorporates therein as a plasticizer thereof the triglyceride compound represented by the general formula (I') which has no toxicity, excels in compatibility with the vinyl chloride type resins, and exhibits ample plasticizing efficiency, it is suitable as a material for medical implements. The shaped articles obtained by molding this material is highly excellent in safety, processibility, flexibility, transparency, and resistance to heat. When they are used as medical implements, therefore, they can manifest their inherent effects to the fullest extent. These effects are manifested particularly conspicuously when the medical implements are destined to contact blood or body fluid.

The vinyl chloride type resins which are usable for the production of the vinyl chloride type resin composition for medical appliances according with the present invention include polyvinylidene chloride, copolymers between not less than 40% by weight, more desirably not less than 65% by weight, and most desirable not less than 75% by weight, of vinyl chloride and other copolymerizable monomer, besides homopolymer of vinyl chloride. The average polymerization degree of the vinyl chloride resin is in the range of 400 to 3,000, more desirably 600 to 2,700, and most desirably 800 to 1,700. Examples of the comonomer usable in combination with the vinyl chloride in the production of the copolymer include vinylidene chloride, ethylene, propylene, vinyl acetate, vinyl bromide, vinyl fluoride, styrene, vinyl toluene, vinyl acetate, vinyl bromide, vinyl fluoride, styrene, vinyl toluene, vinyl pyridine, acrylic acid, alkyl acrylates (such as methyl acrylate, ethyl acrylate, isopropyl acrylate, n-butyl acrylate, and 2-ethylhexyl methacrylate), acrylonitrile, and methacrylonitrile. Optionally, the vinyl chloride resin may incorporate therein styrene-acrylonitrile copolymer or styrene-methacrylonitrile copolymer.

In the vinyl chloride type resin of this kind, the triglyceride compound represented by the general formula (I') is incorporated.

The triglyceride compound represented by the general formula (I') is incorporated in a proportion falling in the range of 5 to 40% by weight, preferably 10 to 35% by weight.

Optionally, the vinyl chloride type resin composition for medical appliances according with the present invention may incorporate therein an epoxidized vegetable oil such as epoxidized soybean oil or epoxidized linseed oil which is useful as a combination stabilizer and auxiliary plasticizer, a methallic soap of calcium or zinc and stearic acid, laurylic acid, ricinolic acid, or naphthenic acid which is useful as a stabilizer, a lubricant, or an antioxidant. The amount of the epoxidized vegetable oil to be incorporated as a combination stabilizer and auxiliary plasticizer is in the range of 2 to 8% by weight, preferably 4 to 6% by weight. The amount of the metallic soap to be incorporated as a stabilizer is in the range of 0.03 to 2% by weight, preferably 0.05 to 1% by weight.

The molding of the vinyl chloride type resin composition for medical appliances according with the present invention can be effected by any of the conventional methods available for vinyl chloride type resin compositions. Examples include calender molding, extrusion molding, and plastisol method. The adhesion of molded parts may be attained by high-frequency fusion or thermal fusion.

Medical Implements Formed with Vinyl Chloride Type Resin Composition for Medical Appliances Incorporating plasticizer The medical implments of the present invention area formed substantially with the vinyl chloride type resin composition having incorporated in a vinyl chloride type resin a plasticizer comprising a triglyceride compound represented by the general formula (I') and possess highly desirable physical properties in terms of safety, processibility, flexibility, transparency, and resistance to heat. The medical implements of the present invention embrace body fluid preserving containers such as blood bags, medical devices such as catheters, transfusion sets, and blood circuits, packages for the aforementioned medical devices, and packages for medicines such as tablets.

Figure 5:
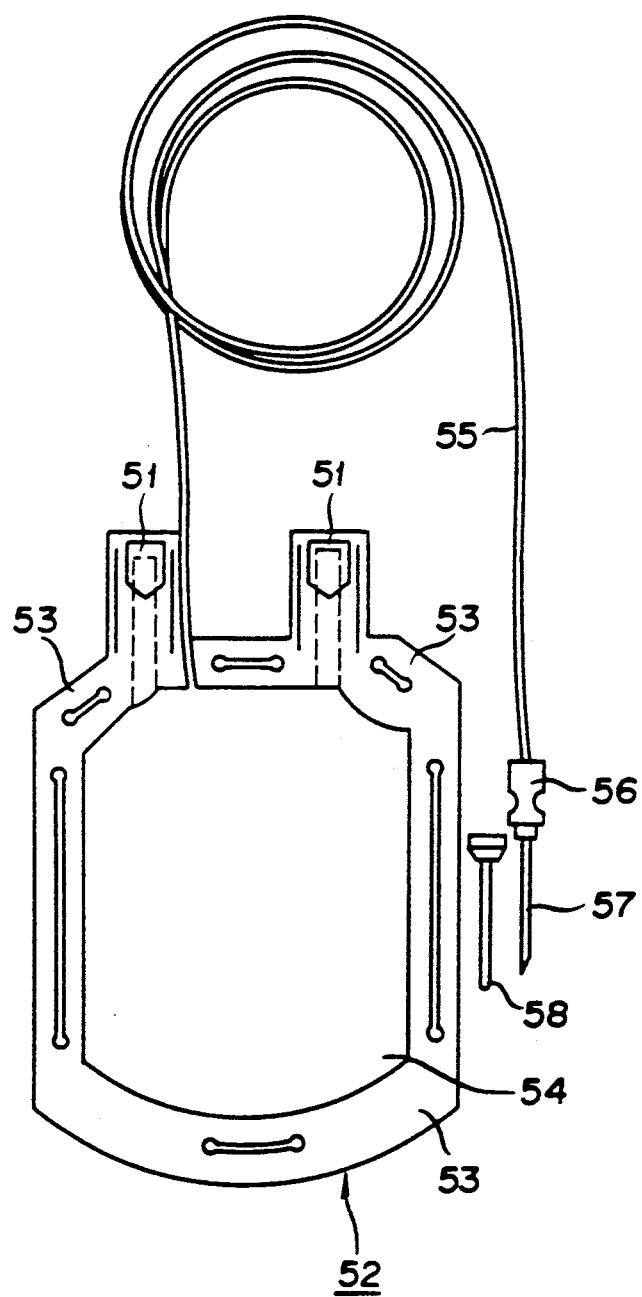
FIG. 5 is a front view illustrating a blood bag as a typical medical implement formed substantially of a vinyl chloride type resin composition for medical appliances incorporating therein a plasticizer as yet another embodiment of the present invention.

Now, a blood bag as a typical medical implement embodying the present invention will be described below with reference to the accompanying drawings. FIG. 5 depicts a blood bag connected to a blood collection needle. A blood bag 52 made of the aforementioned vinyl chloride type resin composition and provided with an outlet 51 fitted with a plurality of peel tabs has a peripheral part 53 thereof heat sealed as by high-frequency heating or other similar heating means. A tube 55 made of the aforementioned vinyl chloride resin composition and adapted to communicate with an inner space 54 of the blood bag 52 is connected to the blood bag 52. The tube 55 is provided at the leading end thereof with a needle base 56, to which a piercing needle 57 is fitted. This piercing needle is protected with a cap 58.

The medical implement of this invention has been described as embodied in a blood bag. Other body fluid preserving containers, medical devices such as catheters, transfusion sets, and blood circuits, packages for such medical devices as mentioned above, and package for medicines such as tablets are formed similarly conveniently with the vinyl chloride type resin composition incorporating therein the plasticizer comprising a triglyceride compound represented by the general formula (I').

The medical implements of the present invention are sterilized before they are put to use. This sterilization is effected chemically with ethylene oxide or physically with an autoclave, for example. Preferably, they are sterilized by autoclaving. In the sterilization by use of an autoclave, medical implements are generally treated at about 121° C. for about 60 minutes. As described above, the medical implements of the present invention possess thermal stability enough to withstand these harsh conditions of the treatment of autoclaving.

EXAMPLE

Now, for the purpose of facilitating the comprehension of this invention, a number of working examples will be cited below. These examples are intended purely as illustrations of the invention and are not meant to limit the scope of this invention in any respect.

EXAMPLE 1

In 2,000 μg/ml of a mixed polyoxyethylene monooleate (guaranteed reagent, produced by Wako Junyaku K.K., and marketed under trademark designation of "Tween 80")/physiological saline glyceryl tri-2-ethylhexanoate (produced by Kao Co., Ltd.) was dispersed in a concentration of 4 mM. In a polypropylene tube fitted with a stopper, 0.2 ml of the resultant emulsion added in a final concentration indicated in Table 1 to a CPD-added human red cell concentrate adjusted in advance to a hematocrit value of about 70% (hereinafter referred to as "CRC") was left standing at rest at 4° C. for 4 weeks. After the standing, the contents of the tube were tested for plasma hemoglobin concentration by the TMB method [Clin. Chem., 23, 749-(1977)]. The results were as shown in Table 1.

Controls 1 and 2

Emulsions were prepared by following the procedure of Example 1, except that di-2-ethylhexyl phthalate (Control 1) and glyceryl di-2-ethylhexanoate (Control 2) were used in place of glyceryl tri-2-ethylhexanoate. They were severally added to CRC and left standing in the tube. After the standing, the contents of the tubes were tested for plasma hemoglobin concentration. The results were as shown in Table 1.

Control 3

The CRC having 2,000 μg/ml of a mixed polyoxyethylene monooleate (guaranteed reagent, produced by Wako Junyaku K.K., and marketed under trademark designation of "Tween 80")/physiological saline solution alone added thereto was left standing in the tube similarly to Example 1. The contents of the tube, after the standing, was tested for plasma hemoglobin concentration. The results were as shown in Table 1.

TABLE 1

| Sample | | Final concentration of sample (μM) | Plasma hemoglobin concentration (mg/dl) |
|---|---|---|---|
| Example 1 | Glyceryl tri-2-ethylhexanoate | 400 | 27 |
| | | 40 | 47 |
| Control 1 | Di-2-ethylhexyl phthalate | 400 | 36 |
| | | 40 | 55 |
| Control 2 | Glyceryl di-2-ethylhexanoate | 400 | 71 |
| | | 40 | 72 |
| Control 3 | — | — | 70 |

EXAMPLE 2

The CRC adjusted to a hematocrit value of about 70% and glyceryl tri-2-ethylhexanoate (produced by Kao Co., Ltd.) added directly thereto in a final concentration indicated in Table 2 were gently stirred. In a tube of polypropylene fitted with a stopper, the resultant mixture was left standing at 4° C. for 4 weeks. At the end of the standing, the contents of the tube were tested for plasma hemoglobin concentration similarly to Example 1. The results were as shown in Table 2.

Controls 4 and 5

Emulsions were prepared by following the procedure of Example 2, excepting di-2-ethylhexyl phthalate (Control 4) and glyceryl di-2-ethylhexanoate (Control 5) were added to the CRC in the place of glyceryl tri-2-ethylhexanoate. The emulsions were left standing at rest and, after the standing, tested for plasma hemoglobin concentration. The results were as shown in Table 2.

Control 6

The CRC was placed in the tube of polypropylene fitted with a stopper and left standing at rest in the same manner as in Example 2. After the standing, the contents of the tube were tested for plasma hemoglobin concentration. The results were as shown in Table 2.

TABLE 2

| Sample | | Final concentration of sample (μM) | Plasma hemoglobin concentration (mg/dl) |
|---|---|---|---|
| Example 2 | Glyceryl tri-2-ethylhexanoate | 400 | 35 |
| | | 40 | 48 |
| Control 4 | Di-2-ethylhexyl phthalate | 400 | 40 |
| | | 40 | 61 |
| Control 5 | Glyceryl di-2-ethylhexanoate | 400 | 72 |
| | | 40 | 85 |
| Control 6 | — | — | 80 |

It is clearly noted from the results that the CRC's having the hemolysis depressant of the present invention, i.e. glyceryl tri-2-ethylhexanoate, added in some form or other were found to possess plasma hemoglobin concentrations (Examples 1 and 2) substantially equal to those of the CRC having di-2-ethylhexyl phthalate added in some form or other (Controls 1 and 4), indicating that they exhibited a highly desirable protective action for erythrocytes.

EXAMPLE 3

A flexible vinyl chloride resin composition using components as shown in Table 3 was roll kneaded at 160° C. for 10 minutes and then molded in the form of a sheet 0.4 mm in thickness with an extruding machine. A miniature blood bag having an inner volume of 20 ml was produced by superposing two such sheets and sealing the superposed sheets by fusing prescribed portions thereof by high frequency heating. About 20 ml of the CRC adjusted in advance to a hematocrit value of about 70% was placed in the bag and left standing at rest at 4° C. for 4 weeks. After the standing, the CRC was tested for plasma hemoglobin concentration in the same manner as in Example 1. The results were as shown in Table 4.

Controls 7 and 8

Miniature blood bags were produced by following the procedure of Example 3, excepting flexible vinyl chloride resin compositions using the same components in different proportions indicated in Table 3 were used instead. The CRC's were left standing at rest in the blood bags and, at the end of the standing, tested for plasma hemoglobin concentration. The results were as shown in Table 4.

TABLE 3

| | Composition (parts by weight) | | |
|---|---|---|---|
| | Example 3 | Control 7 | Control 8 |
| Polyvinyl chloride (average polymerization degree, P = 1,300) | 100 | 100 | 100 |
| Di-2-ethylhexyl phthalate | — | 50 | — |
| Di-normal decyl phthalate | 37 | — | 50 |
| Glyceryl tri-2-ethylhexanoate | 15 | — | — |
| Epoxidized soybean oil | 8 | 8 | 8 |
| Ca/Zn type stabilizer | 0.1 | 0.1 | 0.1 |

TABLE 4

| | Plasma hemoglobin concentration (mg/dl) |
|---|---|
| Example 3 | 47 |
| Control 7 | 46 |
| Control 8 | 133 |

It is clearly noted from the results given above that the CRC preserved in the blood bag formed of the flexible vinyl chloride resin composition incorporating therein the hemolysis depressant of this invention, i.e. glyceryl tri-2-ethylhexanoate (Example 3) was found to possess a plasma hemoglobin concentration substantially equal to the plasma hemoglobin concentration of the CRC preserved in the blood bag formed of the flexible vinyl chloride resin composition incorporating di-2-ethylhexyl phthalate (Control 7), indicating that it exhibited a highly desirable protective action for erythrocytes.

In the CRC of Control 7, the amount of di-2-ethylhexyl phthalate exuded from the blood bag was 250 ppm, whereas the amount of glyceryl tri-2-ethylhexanoate exuded into the CRC of Example 3 was 46 ppm and that of di-normal decyl phthalate was 1 ppm.

EXAMPLE 4

Pellets of a mixture of 100 parts by weight of an ethylene-vinyl acetate copolymer (produced by Mitsubishi Petro-Chemical Co., Ltd. and marketed under trademark designation of "Yukalon EVA") and 20 parts by weight of glyceryl tri-2-ethylhexanoate were produced with a biaxial extruding machine provided with a vent. Sheets were produced by extrusion molding these pellets. A miniature blood bag having an inner volume of 20 ml was produced by superposing two such sheets and sealing the superposed sheets by fusing prescribed portions thereof by high-frequency heating. About 20 ml of a CPD-added human red cell concentrate adjusted in advance to a hematocrit value of about 70% (hereinafter referred to as "CRC") was placed in the blood bag and left standing at rest at 4° C. for 3 weeks. After the standing, the contents of the blood bag were tested for plasma hemoglobin concentration by the TMB method [Clin. Chem., 23, 749- (1977)]. The results were as shown in Table 5.

Control 9

A miniature blood bag was produced by following the procedure of Example 1, except that the ethylene-vinyl acetate copolymer (produced by Mitsubishi Petro-Chemical Co., Ltd. and marketed under trademark designation of "Yukalon EVA") alone was used instead. The CRC was kept standing in the blood bag and, at the end of the standing, tested for plasma hemoglobin concentration in the same manner as in Example 1. The results were as shown in Table 5.

EXAMPLE 5

A miniature blood bag was produced by following the procedure of Example 4, except that polyurethane (produced by Dai-Nippon Ink & Chemicals, Inc. and marketed under trademark designation of "Pandex") was used in the place of the ethylene-vinyl acetate copolymer. The CRC was left standing in the miniature blood bag similarly and, at the end of the standing, tested for plasma hemoglobin concentration. The results were as shown in Table 5.

Control 10

A miniature blood bag was produced by following the procedure of Example 5, except that polyurethane (produced by Dai-Nippon Ink & Chemicals, Inc. and marketed under trademark designation of "Pandex") alone was used instead. The CRC was left standing in this blood bag and, at the end of this standing, tested for plasma hemoglobin concentration. The results were as shown in Table 5.

TABLE 5

| | Flexible resin | Additive | Plasma hemoglobin concentration (mg/dl) |
|---|---|---|---|
| Example 4 | Ethylene-vinyl acetate copolymer | Glyceryl tri-2-ethylhexanoate | 28 |
| Control 9 | Ethylene-vinyl acetate copolymer | — | 92 |
| Example 5 | Polyurethane | Glyceryl tri-2-ethylhexanoate | 30 |
| Control 10 | Polyurethane | — | 95 |

It is clearly noted from the results given in Table 5 that when the flexible resin composition accordingwith this invention was used (Examples 4 and 5), the hemolysis was crubed to a greater extent than when nothing was added to the flexible resin composition (Controls 9 and 10).

EXAMPLE 6

Pellets of a mixture of 100 parts by weight of polyethylene terephthalate (produced by Japan Unipet K.K. and marketed under trademark designation of "Unipet RT560") and 3 parts by weight of grecelyl tri-2-ethylhexanoate were produced by using a biaxial extruding machine provided with a vent. A blood collection tube having an inner volume of 5 ml was produced by injection molding the pellets. In the blood collection tube, about 3 ml of an EDTA-added human blood was left standing at 4° C. for 3 weeks. After the standing, the contents of the blood collection tube were tested for plasma hemoglobin concentration by the TMB method [Clin. Chem., 23 749- (1977)]. The results were as shown in Table 6.

Control 11

A blood collection tube was produced by following the procudure of Example 6, except that pellets formed soley with polyethylene terephthalate (produced by Japan Unipet K.K. and marketed under trademark designation of "Unipet RT 560") were used instead. This blood collection tube was similarly treated. The results were as shown in Table 6.

EXAMPLE 7

A blood collection tube was produced by following the procedure of Example 6, except that polystyrene (produced by Nippon Steel Chemical Co., Ltd. and marketed under trademark designation of "Estyrene G-12F") was used in place of the polyethylene terephthalate. This blood collection tube was similarly treated. The results were as shown in Table 6.

Control 12

A blood collection tube was produced by following the procedure of Example 6, except that polystyrene (produced by Nippon Steel Chemical Co., Ltd. and marketed under trademark designation of "Estyrene G-12F") alone was used instead. The blood collection tube was similarly treated. The results were as shown in Table 6.

EXAMPLE 8

A blood collection tube was produced by following the procedure of Example 6, except that polymethyl methacrylate (produced by Kyowa Gas Chemical Industry Co., Ltd. and marketed under trademark designation of "Parapet G") was used in place of the polyethylene terephthalate. This blood collection tube was similarly treated. The results were as shown in Table 6.

Control 13

A blood collection tube was produced by following the procedure of Example 6, except that pellets formed solely with polyethyl methacrylate (produced by Kyowa Gas Chemical Industry Co., Ltd. and marketed under trademark designation of "Parapet G") were used instead. This blood collection tube was similarly treated. The results were as shown in Table 6.

EXAMPLE 9

A blood collection tube was produced by following the procedure of Example 6, except that polyacrylonitrile (produced by Vestron Co. and marketed under trademark designation of "BAREX 210") was used in place of the polyethylene terephthalate. This blood collection tube was similarly treated. The results were as shown in Table 6.

Control 14

A blood collection tube was produced by following the procedure of Example 6, except that pellets formed solely with polyacrylonitrile (produced by Vestron Co. and marketed under trademark designation of "BAREX 210") were used instead. This blood collection tube was similarly treated. The results were as shown in Table 6.

TABLE 6

| | Rigid resin | Additive | Plasma hemoglobin concentration* (mg/dl) |
|---|---|---|---|
| Example 6 | Polyethylene terephthalate | Glyceryl tri-2-ethylhexanoate | 61 |
| Control 11 | Polyethylene terephthalate | — | 105 |
| Example 7 | Polystyrene | Glyceryl tri-2-ethylhexanoate | 65 |
| Control 12 | Polystyrene | — | 110 |
| Example 8 | Polymethyl methacrylate | Glyceryl tri-2-ethylhexanoate | 60 |
| Control 13 | Polymethyl methacrylate | — | 97 |
| Example 9 | Poly-acrylonitrile | Glyceryl tri-2-ethylhexanoate | 66 |
| Control 14 | Poly-acrylonitrile | — | 120 |

*The value of plasma hemoglobin concentration indicated represents an average of values obtained of three samples.

It is clearly noted from the results given in Table 6 that where the rigid resin composition according with the present invention was used (Examples 6 through 9), the hemolysis was curbed to a greater extent than when the rigid resin composition not containing the triglyceride compound of this invention and entailing virtually no exudation was used (Controls 11 through 14).

EXAMPLE 10

An emulsion was produced by dissolving polyoxyethylene monooleate (guaranteed reagent, produced by Wako Junyaku K.K. and marketed under trademark designation of "Tween 80") in a final concentration of 600 μg/ml in the SAG solution (composed of 140 mM of NaCl, 1.25 mM of glucose) and uniformly dispersing 1.2 mM of glyceryl tri-2-hexanoate in the resultant solution. In a tube of polypropylene fitted with a stopper, 1.0 ml of the emulsion prepared as described above and 2.0 ml of a human red cell concentrate adjusted in advance to a hematocrit value of about 70% were left standing at rest at 4° C. for 5 weeks. After the standing, the contents of the tube were tested for free hemoglobin concentration in plasma by the TMB method [Clin. Chem., 23 749-(1977)]. The results were as shown in Table 7.

EXAMPLE 11

A blood preserving liquid was produced by following the procedure of Example 10, except that the amount of glyceryl tri-2-ethylhexanoate was changed to 0.12 mM. The contents of the tube were tested for free hemoglobin concentration in plasma in the same manner as in Example 10. The results were as shown in Table 7.

Control 15

A blood preserving liquid was prepared by following the procedure of Example 10, except that glyceryl di-2-ethylhexanoate was used as a diglyceride compound in the place of glyceryl tri-2-ethylhexanoate. The change of free hemoglobin concentration in plasma was studied. The results were as shown in Table 7.

Control 16

A blood preserving liquid was prepared by following the procedure of Control 15, except that the amount glyceryl di-2-ethylhexanoate added was changed to 0.12 mM. The change of free hemoglobin concentration in plasma was studied. The results were as shown in Table 7.

Control 17

A blood preserving liquid was prepared by following the procedure of Example 10, except that di-2-ethylhexyl phthalate, a compound well known as possessing a hemolytic activity, was used in the place of glyceryl tri-2-ethylhexanoate. The change of free hemoglobin concentration in plasma was studied by following the procedure of Example 10. The results were as shown in Table 7.

Control 18

A blood preserving liquid was prepared by following the procedure of Control 17, except that the amount of di-2-ethylhexyl phthalte added was changed to 0.12 mM. The change of free hemoglobin concentration in plasma was studied by following the procedure of Control 17. The results were as shown in Table 7.

TABLE 7

|  | Additive | Final concentration of additive in red cell concentrate (mM) | Free hemoglobin concentration in plasma (mg/dl) |
|---|---|---|---|
| Example 10 | Glyceryl tri-2-ethylhexanoate | 400 | 95 |
| Example 11 | Glyceryl tri-2-ethylhexanoate | 40 | 122 |
| Control 15 | Glyceryl di-2-ethylhexanoate | 400 | 218 |
| Control 16 | Glyceryl di-2-ethylhexanoate | 40 | 210 |
| Control 17 | Di-2-ethylhexyl phthalate | 400 | 117 |
| Control 18 | Di-2-ethylhexyl phthalate | 40 | 132 |
| Blank | — | — | 213 |

It is clearly noted from Table 7 that the blood preserving liquid compositions (Examples 10 and 11) incorporating therein triglyceride compounds represented by the general formula (I) according with the present invention manifested as high an antihemolytic activity as those incorporating therein di-2-ethylhexyl phthalate (Controls 17 and 18), whereas those incorporating therein di-2-ethyl-ate, a diglyceride compound not falling within the range of the present invention, (Controls 15 and 16) were found to manifest substantially no antihemolytic activity.

EXAMPLE 12

A test for platelet function recovery was carried out by the following procedure.

A methanolic solution containing glyceryl tri-2-ethylhexanoate in a concentration of 2,000 μg/ml was added to a human platelet poor plasma (hereinafter referred to as "PPP") in a proportion of 1/100 by volume. A mixture of 2 ml of the PPP thus prepared and 1 ml of human platelet rich plasma (PRP) was incubated at 37° C. for 90 minutes. Then, the platelets were washed [Legrand et al., Eur. J. Biochem. 142,465 (1984)], resuspended in Tyrode/BSA solution (Tyrode solution of pH 7.35 containing 2 mM of $CaCl_2$, 1 mM of $MgCl_2$, 5 mM HEPES, and 3.5 mg/ml of BSA solution) having apyrase added thereto in a proportion of 2 μg/ml of protein, and was tested for maximum aggregation capacity with respect to 50 μM of ADP (adenosine diphosphate) and 10 mg/ml of collagen with an instrument (produced by Kyoto Daiichi Kagaku K. K. and marketed under trademark designation of "Aggrecoder") The results are shown in Table 8.

Controls 19 and 20

Two runs of the test for platelet function recovery were carried out by following the procedure of Example 12, except that di-2-ethylhexyl phthalate (Control 19) and di-normal decyl phthalate (Control 2 ) were respectively used in a concentration of 2,000 μg/ml in the place of the methanol solution of glyceryl tri-2-ethylhexanoate. The results were as shown in Table 8.

Control 21

A test for platelet function recovery was carried out by following the procedure of Example 12, except that methanol was used in the place of the methanol solution of glyceryl tri-2-ethylhexyl phthalate. The results were as shown in Table 8.

TABLE 8

|  |  | Maximu aggregation ratio (%) | |
|---|---|---|---|
|  |  | ADP 50 μM | Collagen 10 μg/ml |
| Example 12 | Glyceryl tri-2-ethylhexanoate | 10.4 | 77.9 |
| Control 19 | Di-2-ethylhexyl phthalate | 6.5 | 46.9 |
| Control 20 | Di-normal decyl phthalate | 17.3 | 84.5 |
| Control 21 | — | 12.1 | 85.3 |

As shown in Table 8, di-2-ethylhexyl phthalate was found to manifest a discernible activity to repress the recovery of the platelet aggregation ability. This fact implies that di-2-ethylhexyl phthalate, on entering the human body, possibly impairs the function of platelets. In contrast, glyceryl tri-2-ethylhexanoate used as a hemolysis depressant and di-normal decyl phthalate used as a plasticizer in the present invention were not found to manifest any such repressive activity. The results indicate that they are highly safe substances.

EXAMPLE 13

A vinyl chloride type resin composition made up of the components as indicated in Table 9 was roll kneaded at 150° C. for 5 minutes as indicated in Table 9 was roll kneaded at 150° C. for 5 minutes and press molded at 160° C. under 400 kg/cm for 6 minutes to produce a sheet 0.4 mm in thickness. The sheet was tested for physical properties. The results were as shown in Table 10. The test for 100% modulus and that for tensile strength were carried out by the methods defined in JIS K7113.

When this sheet was sterilized in an autoclave at 121° C. for 60 minutes, it was found to sustain absolutely no deformation.

Control 22

A sheet 0.4 mm in thickness was produced by following the procedure of Example 13, except that a vinyl chloride type resin composition made up of the components as shown in Table 9 was used instead. The sheet was tested for physical properties. The results were as shown in Table 10.

TABLE 9

| Formulation of vinyl chloride type resin composition | | |
|---|---|---|
| Component | Example 13 | Control 22 |
| Vinyl chloride (average polymerization degree, P = 1,300) | 100 | 100 |
| Glyceryl tri-2-ethylhexanoate | 50 | — |
| Di-2-ethylhexyl phthalate | — | 50 |
| Epoxidized soybean oil | 10 | 10 |
| Stabilizer | 1 | 1 |

TABLE 10

| Properties of vinyl chloride type resin composition | | |
|---|---|---|
| | Example 13 | Control 22 |
| 100% modulus (kgf/cm$^2$) | 112 | 100 |
| Tensile strength (kgf/cm$^2$) | 204 | 206 |

It is clearly noted from Table 10 that glyceryl tri-2-ethylhexnoate, a plasticizer according with the present invention manifested as highly desirable compatibility and plasticizing efficiency relative to vinyl chloride resin as 2-ethylhexyl phthalate and the vinyl chloride type resin composition plasticized with this glyceryl tri-2-ethylhexanoate possessed physical properties equal to those of the conventional vinyl chloride type resin composition.

Industrial Appicability

As described above, the hemolysis depressant according with this invention possesses a highly desirable protective activity for erythrocytes and, at the same time, excels in safety. Furthermore, the hemolysis depressant is capable of being to various forms, for example, the form incorporated in a varying synthetic resin composition, and the emulsion form into a varying aqueous medium. The hemolysis depressant is enabled to prevent erythrocytes from hemolysis evenwhen it will be in these forms. Therefore, when the hemolysis depressant of this invention is added to an erythrocyte containing liquid such as whole blood or concentrated red cells, most of the erythrocytes can be retained for a long time in the same state as immediately after blood extraction. Thus, it should be said that the present invention offers distinguished contribusion to various technical fields, including transfusionics clinical analytic as well as medicine.

The plasticizer according with the present invention is substantially non-toxic and exhibits highly desirable compatibility and plasticizing efficiency relative to vinyl chloride type resins. Since the vinyl chloride type resin compositions obtained by incorporating the plasticizer are consequently capable of manifesting outstanding physical properties in terms of safety, moldability, flexibility, transparency, and thermal stability, they contribute greatly to numerous fields, especially in applications to medical appliances and food packages.

We claim:

1. A method for depressing hemolysis during the preservation of blood comprising contacting an erythrocyte containing liquid with a triglyceride compound represented by the general formula (I):

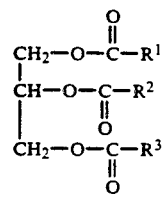

in an effective amount for depressing hemolysis, wherein $R^1$, $R^2$, and $R^3$ are independently each an aliphatic hydrocarbon group of 1 to 20 carbon atoms and the total number of the carbon atoms of $R^1$, $R^2$, and $R^3$ is in the range of 10 to 36.

2. The method according to claim 1, wherein $R^1$, $R^2$ and $R^3$ in said general formula (I) independently stand for an aliphatic hydrocarbon group of 1 to 10 carbon atoms and the total number of the carbon atoms of $R^1$, $R^2$, and $R^3$ is in the range of 10 to 30.

3. The method according to claim 1 or claim 2, wherein at least one of the substituents, $R^1$, $R^2$, and $R^3$ in said general formula (I) possesses a branched structure.

4. The method according to claim 1, wherein said triglyceride compound represented by said general formula (I) is glyceryl tri-2-ethylhexanoate.

5. The method according to claim 1, further comprising directly adding said triglyceride compound to an erythrocyte-containing solution.

6. The method according to claim 5, further comprising adding said triglyceride compound in the form of an emulsion to said erythrocyte-containing solution.

* * * * *